United States Patent
Pillow et al.

(10) Patent No.: US 9,142,782 B2
(45) Date of Patent: Sep. 22, 2015

(54) ORGANIC LIGHT-EMITTING MATERIAL, DEVICE AND METHOD

(75) Inventors: Jonathan Pillow, Cambridgeshire (GB); Torsten Bünnagel, Cambridgeshire (GB); Martina Pintani, Cambridgeshire (GB); Christian Nielsen, London (GB)

(73) Assignees: Cambridge Display Technology, Ltd., Godmanchester (GB); Sumitomo Chemical Company Limited, Tokyo (JP)

(*) Notice: Subject to any disclaimer, the term of this patent is extended or adjusted under 35 U.S.C. 154(b) by 19 days.

(21) Appl. No.: 13/805,268

(22) PCT Filed: Jun. 24, 2011

(86) PCT No.: PCT/GB2011/000950
§ 371 (c)(1),
(2), (4) Date: Apr. 8, 2013

(87) PCT Pub. No.: WO2011/161417
PCT Pub. Date: Dec. 29, 2011

(65) Prior Publication Data
US 2013/0200348 A1 Aug. 8, 2013

(30) Foreign Application Priority Data

| Jun. 25, 2010 | (GB) | 1010741.5 |
| Jun. 25, 2010 | (GB) | 1010742.3 |
| Jun. 25, 2010 | (GB) | 1010743.1 |
| Jun. 25, 2010 | (GB) | 1010745.6 |
| Jan. 31, 2011 | (GB) | 1101642.5 |

(51) Int. Cl.
C08G 79/08 (2006.01)
H01L 51/00 (2006.01)
(Continued)

(52) U.S. Cl.
CPC .......... *H01L 51/0058* (2013.01); *C07C 13/567* (2013.01); *C07C 15/18* (2013.01);
(Continued)

(58) Field of Classification Search
CPC .............. C08L 65/00; C08G 2261/148; C08G 2261/15
USPC .......................................................... 528/8
See application file for complete search history.

(56) References Cited

U.S. PATENT DOCUMENTS

| 3,907,904 A | 9/1975 | Luethi |
| 4,769,304 A | 9/1988 | Kondo et al. |

(Continued)

FOREIGN PATENT DOCUMENTS

| CN | 101016248 A | 8/2007 |
| CN | 101279888 A | 10/2008 |

(Continued)

OTHER PUBLICATIONS

Kuo et al., Journal of Polymer Science: Part A: Polymer Chemistry, vol. 45, 4504-4513, 2007).*

(Continued)

*Primary Examiner* — Liam J Heincer
(74) *Attorney, Agent, or Firm* — Wolf, Greenfield & Sacks, P.C.

(57) ABSTRACT

Composition having an organic semiconducting material and a triplet-accepting material of formula (I) with a triplet energy level lower than the triplet energy level of the organic semiconducting material, in which each Ar is optionally substituted aryl or heteroaryl group, n is 1-3, m is 1-5, q is 0 or 1, each $R^3$ is H or a substituent, and each $R^4$ is H or a substituent. Where $R^4$ is not H, $R^4$ and $(Ar)_m$ bound to the same carbon atom may be linked by a direct bond or a divalent group. Where n or m is at least 2, adjacent Ar groups may be linked by a divalent group. Where q=0, $R^3$ is not H and is linked to $(Ar)_n$ by a direct bond or a divalent group.

18 Claims, 11 Drawing Sheets

(51) Int. Cl.

| | |
|---|---|
| C07C 13/567 | (2006.01) |
| C07C 15/18 | (2006.01) |
| C07C 15/52 | (2006.01) |
| C08G 61/02 | (2006.01) |
| C08G 61/12 | (2006.01) |
| C08L 65/00 | (2006.01) |
| C09K 11/06 | (2006.01) |
| H01L 51/50 | (2006.01) |
| H05B 33/14 | (2006.01) |
| H01L 51/56 | (2006.01) |

(52) U.S. Cl.
CPC .............. *C07C 15/52* (2013.01); *C08G 61/02* (2013.01); *C08G 61/12* (2013.01); *C08G 61/122* (2013.01); *C08L 65/00* (2013.01); *C09K 11/06* (2013.01); *H01L 51/0002* (2013.01); *H01L 51/005* (2013.01); *H01L 51/0032* (2013.01); *H01L 51/0039* (2013.01); *H01L 51/0052* (2013.01); *H01L 51/5012* (2013.01); *H01L 51/5016* (2013.01); *H01L 51/56* (2013.01); *H05B 33/14* (2013.01); *C07C 2103/18* (2013.01); *C08G 2261/148* (2013.01); *C08G 2261/1414* (2013.01); *C08G 2261/15* (2013.01); *C08G 2261/226* (2013.01); *C08G 2261/228* (2013.01); *C08G 2261/312* (2013.01); *C08G 2261/3162* (2013.01); *C08G 2261/3245* (2013.01); *C08G 2261/3422* (2013.01); *C08G 2261/5222* (2013.01); *C08G 2261/95* (2013.01); *C08L 2205/02* (2013.01); *C09K 2211/1416* (2013.01); *C09K 2211/1425* (2013.01); *C09K 2211/1433* (2013.01)

(56) References Cited

U.S. PATENT DOCUMENTS

| | | | | |
|---|---|---|---|---|
| 5,998,045 | A | 12/1999 | Chen et al. | |
| 6,353,083 | B1 | 3/2002 | Inbasekaran et al. | |
| 6,861,502 | B1 | 3/2005 | Towns et al. | |
| 7,205,366 | B2 | 4/2007 | Jaycox et al. | |
| 2001/0053842 | A1* | 12/2001 | Woo et al. | 528/397 |
| 2002/0048688 | A1 | 4/2002 | Fukuoka et al. | |
| 2002/0185635 | A1* | 12/2002 | Doi et al. | 252/582 |
| 2003/0068527 | A1* | 4/2003 | Noguchi et al. | 428/690 |
| 2003/0082404 | A1 | 5/2003 | Sotoyama et al. | |
| 2003/0088043 | A1* | 5/2003 | Huang et al. | 528/25 |
| 2003/0143429 | A1* | 7/2003 | Suzuki et al. | 428/690 |
| 2003/0165716 | A1* | 9/2003 | Samuel et al. | 428/690 |
| 2004/0137263 | A1* | 7/2004 | Burn et al. | 428/690 |
| 2005/0048313 | A1 | 3/2005 | Sotoyama | |
| 2005/0089714 | A1 | 4/2005 | Hatwar et al. | |
| 2005/0095456 | A1 | 5/2005 | Takeda | |
| 2005/0096491 | A1 | 5/2005 | Hashimoto | |
| 2005/0153167 | A1* | 7/2005 | Suzuki et al. | 428/690 |
| 2005/0164029 | A1* | 7/2005 | Burn et al. | 428/690 |
| 2005/0212409 | A1 | 9/2005 | Shi et al. | |
| 2005/0214566 | A1 | 9/2005 | Shi et al. | |
| 2006/0040131 | A1 | 2/2006 | Klubek et al. | |
| 2006/0229427 | A1* | 10/2006 | Becker et al. | 528/86 |
| 2006/0240565 | A1 | 10/2006 | Tang et al. | |
| 2007/0145886 | A1 | 6/2007 | Aziz et al. | |
| 2007/0244295 | A1 | 10/2007 | Fujita | |
| 2009/0066238 | A1* | 3/2009 | Chen et al. | 313/504 |
| 2009/0191428 | A1 | 7/2009 | Hatwar et al. | |
| 2009/0308456 | A1 | 12/2009 | Rand et al. | |
| 2011/0042658 | A1 | 2/2011 | Kobayashi | |
| 2011/0186828 | A1 | 8/2011 | Pillow et al. | |
| 2012/0008068 | A1 | 1/2012 | Doi et al. | 349/69 |
| 2012/0091449 | A1* | 4/2012 | Uetani et al. | 257/40 |
| 2012/0112170 | A1* | 5/2012 | Jen et al. | 257/40 |
| 2012/0116050 | A1 | 5/2012 | Muellen et al. | |
| 2013/0099223 | A1 | 4/2013 | Kobayashi | |
| 2013/0146813 | A1 | 6/2013 | Oshiyama et al. | |
| 2013/0187145 | A1 | 7/2013 | Pegington et al. | |
| 2013/0187146 | A1* | 7/2013 | Pillow et al. | 257/40 |
| 2013/0187147 | A1 | 7/2013 | King et al. | |
| 2013/0270535 | A1 | 10/2013 | Pillow et al. | |
| 2014/0103303 | A1* | 4/2014 | Carroll | 257/40 |

FOREIGN PATENT DOCUMENTS

| | | |
|---|---|---|
| CN | 101624441 A | 1/2010 |
| EP | 1 359 790 A2 | 11/2003 |
| EP | 1 440 959 A1 | 7/2004 |
| EP | 1 487 027 A2 | 12/2004 |
| FR | 2151005 A1 | 4/1973 |
| GB | 2456788 A | 7/2009 |
| GB | 2463040 A | 3/2010 |
| JP | 2000-164359 A | 6/2000 |
| JP | 2006-243626 A | 9/2006 |
| JP | 2006-253221 A | 9/2006 |
| WO | WO 00/55927 A1 | 9/2000 |
| WO | WO 01/83410 A1 | 11/2001 |
| WO | WO 2005/043640 A2 | 5/2005 |
| WO | WO 2010/013006 A2 | 2/2010 |

OTHER PUBLICATIONS

International Search Report and Written Opinion mailed Sep. 29, 2011 for International Application No. PCT/GB2011/000961.
International Preliminary Report on Patentability mailed Jan. 10, 2013 for International Application No. PCT/GB2011/000961.
International Search Report and Written Opinion mailed Jan. 20, 2012 for International Application No. PCT/GB2011/000949.
International Preliminary Report on Patentability mailed Jan. 10, 2013 for International Application No. PCT/GB2011/000949.
International Search Report and Written Opinion mailed Sep. 27, 2011 for International Application No. PCT/GB2011/000962.
International Preliminary Report on Patentability mailed Jan. 10, 2013 for International Application No. PCT/GB2011/000962.
International Search Report and Written Opinion mailed Sep. 27, 2011 for International Application No. PCT/GB2011/000950.
International Preliminary Report on Patentability mailed Jan. 10, 2013 for International Application No. PCT/GB2011/000950.
Office Communication for EP 11744049.5 mailed Nov. 20, 2014.
Exam Report for corresponding European application No. 11744049.5, dated Apr. 2, 2014, pp. 1-11.
Becker et al., Optimisation of polyfluorenes for light emitting applications. Synthetic Metals. 2001;125(1):73-8.
Bernius et al., Progress with Light-Emitting Polymers. Advanced Materials. 2000;12(23):1737-50.
CAS Registry No. 31927-64-7.
Chen et al., Connector Effect in Electroluminescent Properties of Poly(p-phenylene vinylene) Derivatives Containing Triazole Chromophores. Macromolecular Chemistry and Physics. 2006;207(12):1070-9.
Chen et al., White organic light-emitting devices with a bipolar transport layer between blue fluorescent and orange phosphorescent emitting layers. Applied Physics Letters. 2007; 91:023505. 3 pages.
Ego et al., Attaching perylene dyes to polyfluorene: three simple, efficient methods for facile color tuning of light-emitting polymers. J Am Chem Soc. Jan. 15, 2003;125(2):437-43.
Kang et al., Very large electro-optic coefficients from in situ generated side-chain nonlinear optical polymers. Appl Phys Lett. 2005;87:71109.
Klärner et al., Exciton Migration and Trapping in Copolymers Based on Dialkylfluorenes Advanced Materials. 1999;11(2):115-9.
Lee et al., Investigation of Blue Organic Light-Emitting Diodes (OLEDs) with Various Hosts. J Korean Phys Soc. 2006;49(3):1052-6.
Lee et al., Color tuning in polyfluorenes by copolymerization with low band gap comonomers. Synthetic Metals. 1999;102(1-3):1087-8.
Liu et al., Molecular Design on Highly Efficient White Electroluminescence from a Single-Polymer System with Simultaneous Blue, Green, and Red Emission. Advanced Materials. 2007;19(4):531-5.

(56) References Cited

OTHER PUBLICATIONS

Mills et al., Dications of fluorenylidenes. Relationship between electrochemical oxidation potentials and antiaromaticity in diphenyl-substituted fluorenyl cations. J Org Chem. Apr. 5, 2002;67(7):2003-12.

Peng et al., Study on the energy transfer and luminescent properties in PVK: DBVP blend system. Acta Phys Sin. 2006;55(10):5495-8.

Popovic et al., Delayed Electroluminescence in Small Molecule Based Organic Light Emitting Diodes—Evidence for Triplet-Triplet Annihilation and Recombination Center Mediated Light Generation Mechanism. J App Phys. 2005;98:013510-5.

Shi et al., Anthanthrene Derivatives for Stable Blue-Emitting Organic Electroluminescent Devices. SID 05 Digest. 2005;36:1760-3.

Staroske et al., Single-step triplet-triplet annihilation: an intrinsic limit for the high brightness efficiency of phosphorescent organic light emitting diodes. Phys Rev Lett. May 11, 2007;98(19):197402. Epub May 10, 2007.

Thirunavukkarasu et al., One-Pot Synthesis of Diarylmethylidenefluorenes and Phenanthrenes by Palladium-Catalyzed Multiple C—H Bond Functionalization. Chemistry—A European Journal. 2010;16(5):1436-40.

* cited by examiner

ORGANIC LIGHT-EMITTING MATERIAL, DEVICE AND METHOD

RELATED APPLICATIONS

The present application is a national stage filing under 35 U.S.C. §371 of international PCT application, PCT/GB2011/000950, filed Jun. 24, 2011, which claims priority to United Kingdom patent application, GB 1010741.5, filed Jun. 25, 2010, United Kingdom patent application, GB 1010742.3, filed Jun. 25, 2010, United Kingdom patent application, GB 1010743.1, filed Jun. 25, 2010, United Kingdom patent application, GB 1010745.6, filed Jun. 25, 2010, and United Kingdom patent application, GB 1101642.5, filed Jan. 31, 2011, each of which is incorporated herein by reference.

SUMMARY OF THE INVENTION

This invention relates to organic light emitting compositions, devices containing the same, methods of making said devices, and organic compounds therefor.

BACKGROUND OF THE INVENTION

Electronic devices comprising active organic materials are attracting increasing attention for use in devices such as organic light emitting diodes, organic photovoltaic devices, organic photosensors, organic transistors and memory array devices. Devices comprising organic materials offer benefits such as low weight, low power consumption and flexibility. Moreover, use of soluble organic materials allows use of solution processing in device manufacture, for example inkjet printing or spin-coating.

A typical organic light-emissive device ("OLED") is fabricated on a glass or plastic substrate coated with a transparent anode such as indium-tin-oxide ("ITO"). A layer of a thin film of at least one electroluminescent organic material is provided over the first electrode. Finally, a cathode is provided over the layer of electroluminescent organic material. Charge transporting, charge injecting or charge blocking layers may be provided between the anode and the light-emitting layer and/or between the cathode and the light-emitting layer.

In operation, holes are injected into the device through the anode and electrons are injected into the device through the cathode. The holes and electrons combine in the organic light-emitting layer to form an excitons which then undergo radiative decay to give light.

In WO90/13148 the organic light-emissive material is a conjugated polymer such as poly(phenylenevinylene). In U.S. Pat. No. 4,539,507 the organic light-emissive material is of the class known as small molecule materials, such as tris-(8-hydroxyquinoline) aluminium ("Alq$_3$"). These materials electroluminesce by radiative decay of singlet excitons (fluorescence) however spin statistics dictate that up to 75% of excitons are triplet excitons which undergo non-radiative decay, i.e. quantum efficiency may be as low as 25% for fluorescent OLEDs—see, for example, Chem. Phys. Lett., 1993, 210, 61, Nature (London), 2001, 409, 494, Synth. Met., 2002, 125, 55 and references therein.

It has been postulated that the presence of triplet excitons, which may have relatively long-lived triplet excited states, can be detrimental to OLED lifetime as a result of triplet-triplet or triplet-singlet interactions ("lifetime" as used herein in the context of OLED lifetime means the length of time taken for the luminance of the OLED at constant current to fall by a selected percentage (for example 10% or 50%) from an initial luminance value, and "lifetime" as used herein in the context of lifetime of a triplet excited state means the half-life of a triplet exciton). US 2007/145886 discloses an OLED comprising a triplet-quenching material to prevent or reduce triplet-triplet or triplet-singlet interactions.

U.S. Pat. No. 5,121,029 discloses an electroluminescent device comprising light-emitting materials including distyrylbenzenes.

US 2005/208322 discloses an OLED comprising a light-emitting layer with light emission from 4,4'-bis(2,2' diphenyl vinyl)-1,1'-biphenyl (DPVBi).

Polymer (Korea) 2002, 26(4), 543-550 discloses a polymer host blended with DPVBi as emitter. OLEDs have great potential for display and lighting applications. However, there remains a need to improve performance of these devices.

SUMMARY OF THE INVENTION

The present inventors have identified compounds that provide effective triplet acceptance and quenching in OLEDs.

In a first aspect the invention provides a composition comprising an organic semiconducting material and a triplet-accepting material of formula (I) having a triplet energy level lower than the triplet energy level of the organic semiconducting material:

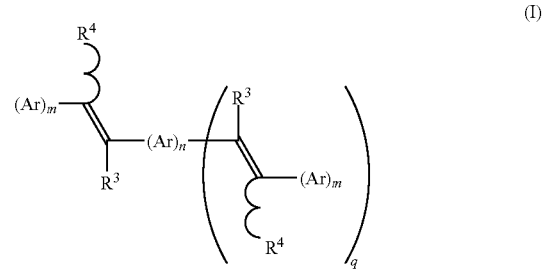

(I)

wherein each Ar independently represents an optionally substituted aryl or heteroaryl group; n is 1-3; m in each occurrence is independently 1-5; q is 0 or 1; each $R^3$ is independently selected from H or a substituent; each $R^4$ is independently selected from H or a substituent; in the case where $R^4$ is not H, $R^4$ and $(Ar)_m$ bound to the same carbon atom may be linked by a direct bond or a divalent group; in the case where $R^3$ is not H, $R^3$ independently in each occurrence and $(Ar)_n$ may be linked by a direct bond or a divalent group; and adjacent Ar groups may be linked by a divalent group in the case where n or m is at least 2, with the proviso that, in the case where q=0, $R^3$ is not H and is linked to $(Ar)_n$ by a direct bond or a divalent group.

Optionally, the organic semiconducting material is selected from a fluorescent light-emitting material; a hole transporting material; an electron transporting material; a hole blocking material; and an electron blocking material.

Optionally, the organic semiconducting material is a polymer, optionally a light-emitting polymer comprising fluorescent light-emitting repeat units.

In one optional arrangement, the composition comprises a blend of the organic semiconducting material and the triplet-accepting material.

In another optional arrangement, the triplet-accepting material is chemically bound to the organic semiconducting material or, if present, to another component of the composition.

Optionally, the triplet-accepting material is bound in the main chain of the polymer or bound as a side group or end group of the polymer.

Optionally, q=1.

Optionally, each $R^3$ is H

Optionally, each $R^4$ is H or —$(Ar)_m$.

Optionally, q=0.

Optionally, $R^3$ is $(Ar)_n$

Optionally, n is 1 or 2.

Optionally, the divalent linking group linking any of adjacent Ar groups; $R^4$ and $(Ar)_m$; and $R^3$ and $(Ar)_n$ is selected from —$(CR^5R^6)_p$—, —$(SiR^5R^6)_p$—, O, $NR^5$ and $PR^5$, wherein $R^5$ and $R^6$ are each independently selected from H or a substituent and p is 1-5, preferably 1 or 2.

Optionally, at least one Ar group, preferably all Ar groups, are phenyl.

Optionally, $R^3$ and/or $R^4$ are phenyl.

Optionally, q=0, n=1, $R^3$ is phenyl, and $R^3$ and $(Ar)_n$ are linked by a direct bond.

Optionally, $R^3$ and $(Ar)_n$ are linked to form an optionally substituted fluorene.

Optionally, $R^5$ and $R^6$ are each independently selected from H or a substituent selected from the group consisting of:
- alkyl wherein one or more non-adjacent C atoms may be replaced with O, S, substituted N, C=O and —COO— and wherein one or more H atoms may be replaced with F; or
- aryl, heteroaryl, arylalkyl or heteroarylalkyl, each of which may optionally be substituted with halogen, cyano, or alkyl wherein one or more non-adjacent C atoms may be replaced with O, S, substituted N, C=O and —COO—.

Optionally, at least one Ar group is substituted with at least one substituent selected from halogen; cyano; alkyl wherein one or more non-adjacent C atoms may be replaced with O, S, substituted N, C=O and —COO—; and —$(Ar^4)_z$, wherein $Ar^4$ in each occurrence is independently selected from optionally substituted aryl or heteroaryl and z is at least 1, optionally 1, 2 or 3, and wherein a plurality of Ar4 groups may be linked to form a straight or branched chain of $Ar^4$ groups in the case where z is greater than 1. Optionally, at least one meta-position of at least one terminal Ar group is substituted with the at least one substituent.

Optionally, the organic semiconducting material comprises an amine.

Optionally, the organic semiconducting material is a polymer comprising amine repeat units.

Optionally, the triplet-accepting material is present in an amount of at least 0.05 mol %, optionally 0.1 mol %, relative to the organic semiconducting material.

In a second aspect the invention provides a solution comprising a solvent and a composition according to the first aspect of the invention.

In a third aspect the invention provides an organic light-emitting device comprising an anode, a cathode, a light-emitting layer between the anode and cathode, and optionally one or more layers selected from charge transporting and charge-blocking layers between the anode and cathode, wherein at least one of the light-emitting layer and the one or more optional layers comprises a composition according to the first aspect.

In a fourth aspect the invention provides a method of forming an organic light-emitting device according to the third aspect comprising the steps of depositing the composition according to the second aspect and evaporating the solvent.

In a fifth aspect the invention provides use of an optionally substituted material of formula (I) for acceptance of triplet excitons generated by a organic semiconducting material in a composition comprising the triplet-accepting unit and the light-emitting material:

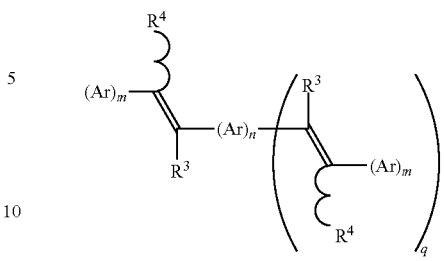
(I)

wherein Ar, n, m, q, $R^3$ and $R^4$ are as described above; in the case where $R^4$ is not H, $R^4$ and $(Ar)_m$ may be linked by a direct bond or a divalent group; in the case where $R^3$ is not H, $R^3$ and $(Ar)_n$ may be linked by a direct bond or a divalent group; and adjacent Ar groups may be linked by a divalent group in the case where n or m is at least 2, with the proviso that, in the case where q=0, $R^3$ is not H and is linked to $(Ar)_n$.

The material of the fifth aspect may be as described with reference to the first aspect of the invention, and may be used as a triplet-absorbing material in a composition with an organic semiconducting material as described with reference to the first aspect.

Optionally according to the fifth aspect, the composition comprises a physical mixture of the organic semiconducting material and the material of formula (I).

Optionally according to the fifth aspect, the material of formula (I) is chemically bound to the organic semiconducting material.

Optionally according to the fifth aspect, the organic semiconducting material is a polymer and the material of formula (I) is bound in the main chain of the polymer or bound as a side group or end group of the polymer.

Optionally according to the fifth aspect, the material of formula (I) quenches triplet excitons generated by the organic semiconducting material.

Optionally according to the fifth aspect, the material of formula (I) mediates triplet-triplet annihilation of triplet excitons transferred from the organic semiconducting material to the triplet-accepting unit.

In a sixth aspect the invention provides a light-emitting composition comprising a polymer and a light emitting unit of formula (Ia):

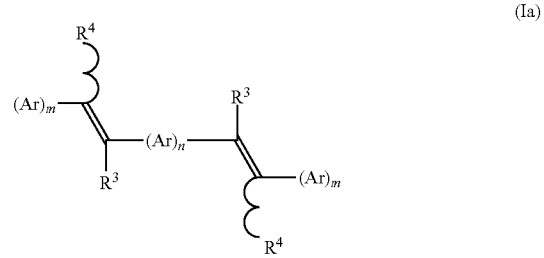
(Ia)

wherein Ar, n, m, $R^3$ and $R^4$ are as described above, and adjacent Ar groups may be linked by a divalent group in the case where n or m is at least 2.

Optionally according to the sixth aspect, the composition comprises a blend of the polymer and the material of formula (I).

Optionally according to the sixth aspect, the material of formula (I) is bound in the main chain of the polymer or bound as a side group or end group of the polymer.

In a seventh aspect the invention provides an organic light-emitting device comprising a light-emitting composition according to the sixth aspect.

In an eighth aspect the invention provides a compound of formula (Ia):

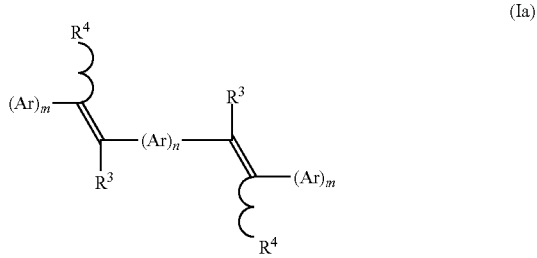

(Ia)

wherein Ar, n, m, $R^3$ and $R^4$ are as defined in any one of claims 1 and 6-13 and adjacent Ar groups may be linked by a divalent group in the case where n or m is at least 2, and wherein at least one terminal aryl group is substituted with a solubilising substituent.

Optionally according to the eighth aspect the compound has a solubility of at least 10 mg/ml in toluene.

Optionally according to the eighth aspect at least one terminal aryl group is a phenyl and at least one said solubilising substituent is located at a meta position of the phenyl.

Optionally according to the eighth aspect the compound has formula (II):

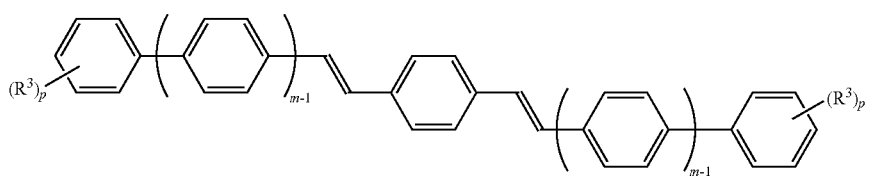

(II)

wherein at least one $R^3$ is straight chain or branched alkyl or alkoxy, preferably alkyl.

In a ninth aspect the invention provides a compound of formula (VI):

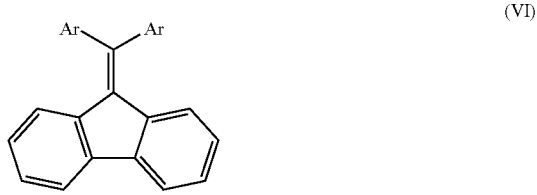

(VI)

wherein each Ar independently represents an aryl or heteroaryl group and wherein the compound may optionally be substituted with one or more substituents.

Optionally, the material of the ninth aspect may be used as a triplet-absorbing material in a composition with an organic semiconducting material as described with reference to the first aspect.

Optionally according to the ninth aspect, the one or more substituents are each independently selected from alkyl wherein one or more non-adjacent C atoms may be replaced with O, S, substituted N, C═O and —COO— and one or more H atoms of the alkyl group may be replaced with F; and —$(Ar^4)_z$, wherein $Ar^4$ in each occurrence is independently selected from optionally substituted aryl or heteroaryl and z is at least 1, optionally 1, 2 or 3, and wherein a plurality of Ar4 groups may be linked to form a straight or branched chain of $Ar^4$ groups in the case where z is greater than 1.

Optionally according to the ninth aspect, each Ar is optionally substituted phenyl.

In a tenth aspect the invention provides a polymer comprising a repeat unit comprising a compound according to the ninth aspect.

Optionally according to the tenth aspect, the repeat unit comprises formula (VIIa) or (VIIb):

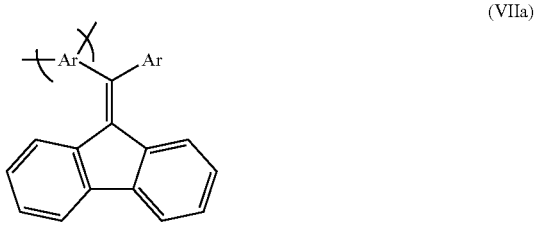

(VIIa)

-continued

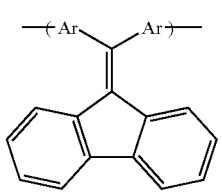

(VIIb)

Optionally, the compound of the ninth aspect is substituted with at least one substituent capable of participating in metal catalysed cross-coupling. Optionally, this substituent is selected from boronic acid and esters thereof, sulfonic acid esters, and halogen, preferably bromine or iodine. Optionally, the substituted compound has formula (VIIIa) or (VIIIb):

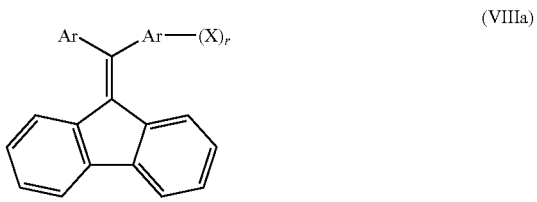

(VIIIa)

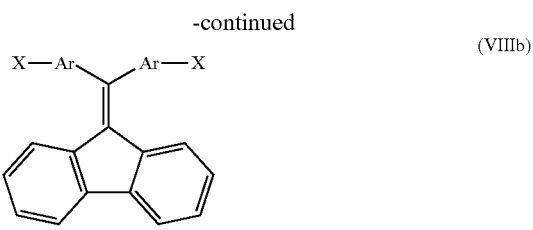

(VIIIb)

wherein each X independently represents the at least one substituent capable of participating in metal-catalysed cross-coupling and r is 1 or 2.

In an eleventh aspect the invention provides a method of forming a polymer according to tenth aspect comprising the step of polymerising a compound of formula (VIIIa) wherein r is 2 or a compound of formula (VIIIb) in the presence of a metal catalyst.

It will be appreciated that the invention in its first aspect relates to a composition wherein the triplet-accepting unit of formula (I) emits substantially no light. The excited singlet state energy level ($S^1$) of the light-emitting material is no higher than, and preferably lower than, the corresponding energy level of triplet-accepting unit in order to prevent any substantial transfer of singlet excitons from the $S^1$ energy level of the light-emitting material to the $S^1$ level of the triplet-accepting material.

The opposite is the case in the second aspect of the invention, wherein the unit of formula (I) is the light-emitting material.

"Aryl" and "heteroaryl" as used herein includes both fused and unfused aryl and heteroaryl groups respectively.

"Triplet accepting unit" as used herein means a unit capable of receiving triplet excitons from the light emitting unit. In order to function efficiently, the triplet accepting unit has a triplet excited state energy level $T^1$ that is lower in energy than that of the light-emitting unit.

$R^3$ and $R^4$ attached to opposite ends of a double bond in compounds of formula (I) may independently in each case be in a cis- or trans-arrangement, as illustrated by the wavy bond of formula (I).

DETAILED DESCRIPTION OF THE INVENTION

The invention is described in detail hereinafter with respect to (A) compositions wherein the compound of formula (I) is a triplet-accepting material, and (B) compositions wherein the compound of formula (I) is a light-emitting material.

A. Triplet-Acceptance by Compounds of Formula (I)

The present inventors have identified a number of pathways by which triplet excitons may be caused to undergo decay in order to reduce or eliminate decay by pathways that cause a drop in device lifetime. This includes pathways in which triplet excitons decay non-radiatively by a quenching process and pathways in which triplet excitons undergo triplet-triplet annihilation, resulting in delayed fluorescence that can provide for better device efficiency as compared to non-radiative quenching pathways.

Without wishing to be bound by any theory, the mechanisms of triplet quenching and delayed fluorescence believed to occur are described below.

Triplet Quenching

Figure 1:
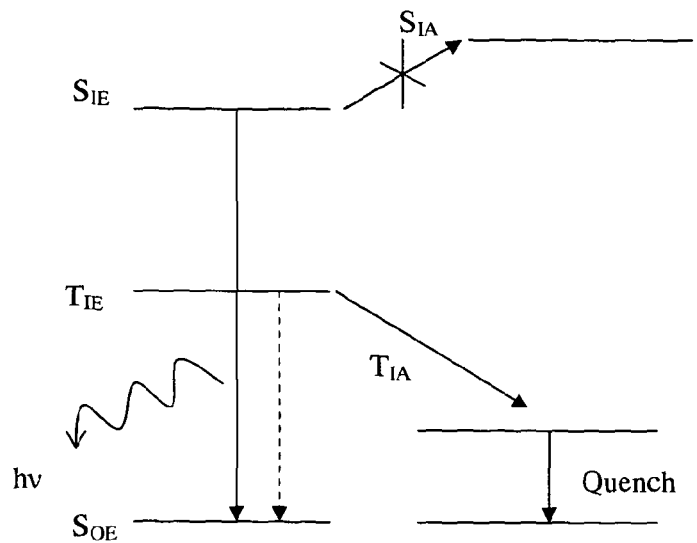
FIG. 1 is a schematic illustration of triplet quenching by a compound of formula (I)

FIG. 1 illustrates a first energy transfer mechanism for an exemplary OLED. For the avoidance of any doubt energy level diagrams herein, including FIG. 1, are not drawn to any scale. FIG. 1 illustrates energy transfer for an OLED provided with a light emitting material having a singlet excited state energy level $S_{1E}$ and a singlet ground state energy level $S_{0E}$. Singlet excitons having energy $S_{1E}$ decay by emission of fluorescent light hv illustrated by the solid arrow between $S_{1E}$ and $S_{0E}$ in FIG. 1. Triplet-triplet exciton interactions or triplet-singlet exciton interactions may create "super-excited" states on the light-emitting material. Without wishing to be bound by any theory, it is believed that formation of these highly energetic "super-excited" states on the light emitting material may be detrimental to operational lifetime of the material. However, by providing a triplet accepting unit having an excited triplet state energy level $T_{1A}$ that is lower than $T_{1E}$, it is possible for triplet excitons to be transferred for quenching to the triplet accepting unit, the alternative of radiative decay from $T_{1E}$ to $S_{0E}$, illustrated by a dotted line in FIG. 1, being a spin-forbidden process.

$S_1$ and $T_1$ levels can be measured from the fluorescence and phosphorescence spectra respectively.

The triplet accepting unit has a singlet excited state energy level $S_{1A}$ that is higher than the singlet excited state energy level $S_{1E}$ in order to substantially or completely prevent transfer of singlet excitons from $S_{1E}$ to $S_m$. Preferably, $S_{1A}$ is at least kT higher in energy than $S_{1E}$ in order to prevent any substantial back-transfer of excitons. Likewise, $T_{1E}$ is preferably at least kT higher in energy than $T_{1A}$.

Triplet-Triplet Annihilation

Figure 2:
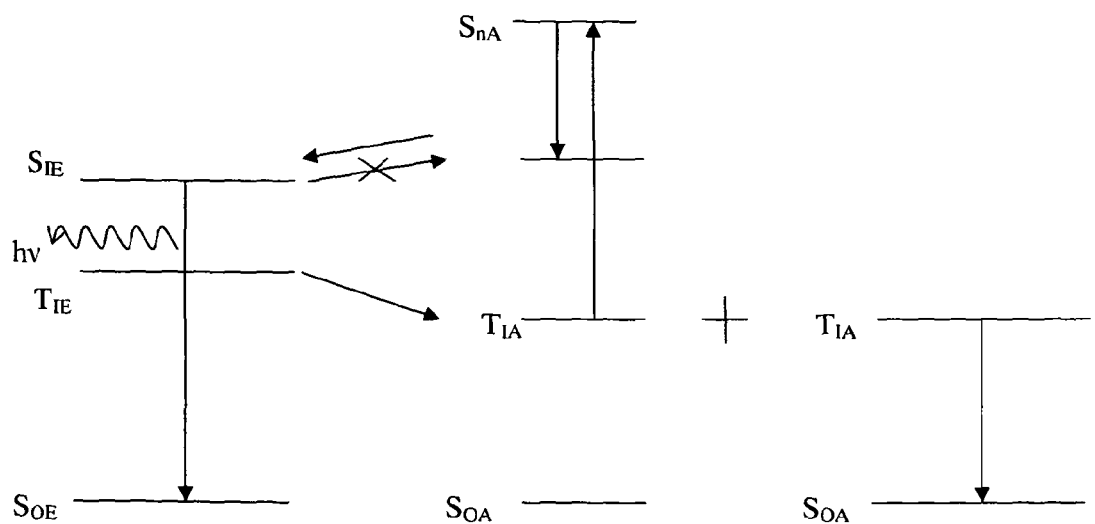
FIG. 2 is a schematic illustration of a first triplet-triplet annihilation mechanism involving a by a compound of formula (I)

FIG. 2 illustrates a second energy transfer mechanism for an exemplary OLED.

According to this embodiment, triplet-triplet annihilation (TTA), caused by an interaction between two triplet-accepting units, results in a triplet-triplet annihilated singlet exciton having an energy of up to $2 \times T_{1A}$, wherein $T_{1A}$ represents the triplet excited state energy level of the triplet-accepting material. This singlet exciton, formed on a first of the two triplet-accepting units, has energy level $S_{nA}$ that is higher in energy than $S_{1A}$ and $S_{1E}$ and so it may transfer to $S_{1A}$ and then to $S_{1E}$ from which light hv may be emitted as delayed fluorescence. The triplet exciton on the second of the two triplet-accepting units may decay to the ground state $T_{OA}$.

Initially, the triplet exciton formed at $T_{1E}$ is transferred to $T_{1A}$. By providing a triplet-accepting material having energy level $T_{1A}$ that is lower than $T_{1E}$, rapid transfer of excitons from $T_{1E}$ to $T_{1A}$ may occur. This transfer is relatively rapid compared to the rate of decay of triplet excitons from $T_{1E}$ to $S_{OE}$, illustrated by a dotted arrow in FIG. 1, which is a spin-forbidden process. The energy gap between $T_{1E}$ and $T_{1A}$ is preferably greater than kT in order to avoid back-transfer of excitons from $T_{1A}$ to $T_{1E}$. Likewise, the energy gap between $S_{1A}$ and $S_{1E}$ is preferably greater than kT in order to avoid back-transfer of excitons from $S_{1E}$ to $S_{1A}$.

A pathway for decay of the triplet exciton on $T_{1A}$ in competition with triplet-triplet annihilation is the non-radiative (quenching) pathway to $S_{OA}$ described above with reference to FIG. 1. A number of measures may be taken to maximise the probability of TTA rather than decay to $S_{OA}$, in particular:

i) The triplet-absorbing material may be selected such that triplet excitons on $T_{1A}$ have a relatively long lifetime $\tau_{1A}$. A relatively long lifetime not only means that the rate of decay to $S_{OA}$ is relatively slow but also that the likelihood of TTA is relatively high.

ii) The concentration of triplet-absorbing material in the light-emitting layer may be relatively high, for example greater than 1 mol %, for example in the range of 0.1-10 mol %, or in the range of 1-10 mol %.

iii) Two or more triplet-accepting materials may be provided in close proximity, for example as described below with reference to units of formula (II).

Each of these measures may be used alone or in combination.

Figure 3:
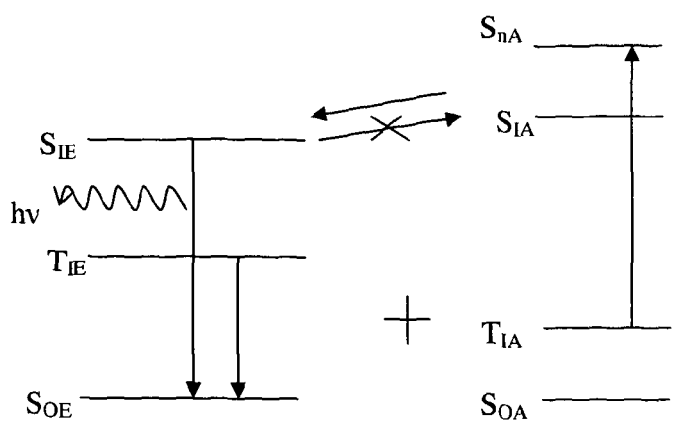
FIG. 3 illustrates a second triplet-triplet annihilation mechanism involving a by a compound of formula (I)

FIG. 3 illustrates a third energy transfer mechanism for an exemplary OLED.

In this case, triplet-triplet annihilation occurs between the triplet exciton of energy $T_{1A}$ located on the triplet accepting triplet-accepting unit and the triplet exciton of energy $T_{1E}$ located on the light-emitting material. It will be appreciated that this results in a triplet-triplet annihilated singlet exciton (TTAS) having an energy of up to $T_{1E}+T_{1A}$. This singlet exciton's energy level of $S_{nA}$ is higher in than that of $S_{1E}$ and so it may transfer its energy to $S_{1A}$ and from there to $S_{1E}$ from which light hv may be emitted as delayed fluorescence.

By avoiding triplet quenching via quenching sites formed during OLED driving, lifetime of the device may be improved. Moreover, by utilising TTA to produce stable, delayed fluorescence it is possible to improve efficiency as compared to a device in which all triplet excitons are quenched (as illustrated in FIG. 1) or as compared to a device in which there is no triplet accepting unit wherein intensity of delayed fluorescence may drop sharply following initial OLED driving.

It will be appreciated that it is possible for two or all three of the triplet-quenching mechanism and the two TTA mechanisms described above to occur within the same device, and that the amount of delayed fluorescence from each of the TTA two mechanisms will depend on factors such as the concentration of light emitting material, the concentration of triplet accepting units and the excited state lifetime of triplet excitons on the light emitting unit and the triplet accepting unit.

Although the long lifetime of the triplet exciton residing on the triplet accepting unit may serve to increase the probability of TTA occurring, either by annihilation with a triplet exciton resident on another triplet accepting unit or by annihilation with a triplet exciton resident on the light-emitting material, other measures may be employed to yet further increase the likelihood of TTA.

For instance, the triplet accepting units may be provided in close proximity, optionally separated by a spacer, in order to increase the likelihood of TTA.

Alternatively, or additionally, the triplet accepting units may be provided in high concentration in order to increase the likelihood of TTA.

The rate constant for transfer of triplet excitons from the light-emitting material to the triplet-accepting material may be selected so as to be greater than the rate constant for transfer of quenching of triplet excitons.

In addition to, or as an alternative to, use of triplet accepting materials in a light-emitting layer of an OLED, triplet accepting materials of formula (I) may be provided in a charge transporting or charge blocking OLED layer. For example, triplet excitons may form within, or migrate into, a hole transporting layer and cause degradation of a hole transporting material of the hole transporting layer. A triplet accepting material of formula (I) may be provided in the hole transporting material for quenching of these triplet excitons. For the purpose of illustration, compositions comprising a triplet accepting material of formula (I) and a light-emitting material are described in more detail below, however the triplet accepting material may equally be used in combination with a charge-transporting material (for example, a hole transporting or electron transporting material) that does not luminesce when in use in an OLED.

Triplet-Accepting Material

The triplet-accepting material may be a compound that is chemically unbound to, but physically blended with, the light-emitting material, and the light-emitting composition may comprise one or more further components, for example one or more charge transporting materials, in particular one or more hole transporting or electron transporting materials. Alternatively, the triplet-accepting material may be bound to the light-emitting material, or to any of the aforementioned other components, where present.

In the case where the triplet-accepting material is blended with the light-emitting material, it is preferably substituted with solubilising groups. Exemplary triplet-accepting compounds include compounds having the following general formula (II):

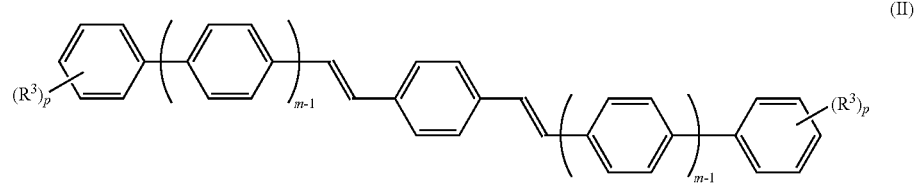

(II)

wherein m is as described above; p is 1-5, preferably 1 or 2; and $R^3$ is independently in each occurrence H or a solubilising substituent, with the proviso that at least one $R^3$ is a solubilising substituent. Preferred solubilising substituents are straight chain or branched alkyl or alkoxy, preferably alkyl.

Two specific examples of such compounds are illustrated below:

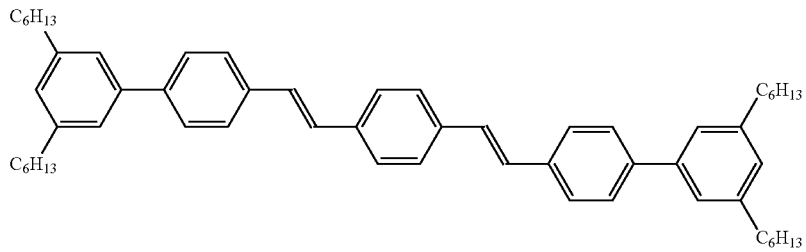

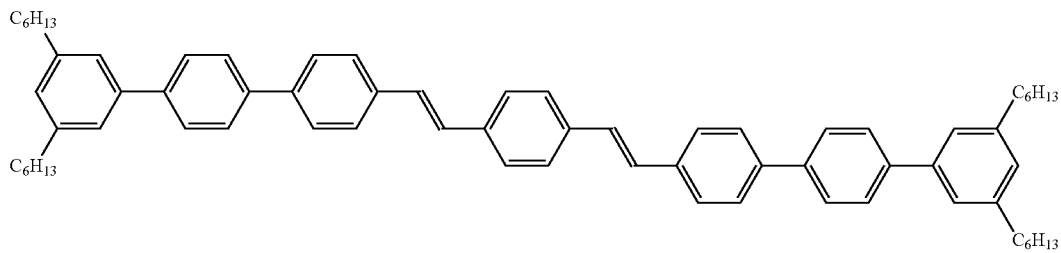

Solubilising substituents in the meta-position of terminal aryl groups may be particularly advantageous for improved solubility.

Adjacent aryl groups may be linked, as shown in the example below wherein adjacent phenyl groups are linked to form a fluorene unit. The bridging carbon atom of the fluorene unit may be provided with substitutents to adjust the solubility, glass transition temperature or other properties of the compound.

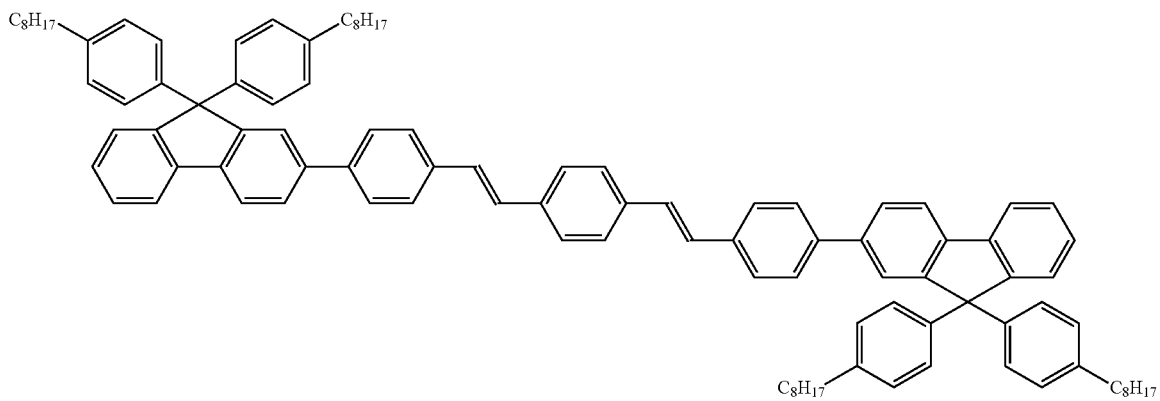

In the examples above, each carbon atom of the double-bond carries only one substituent. However, one or more of these carbon atoms may carry two substituents, as shown in the compound 4,4'-bis(2,2' diphenyl vinyl)-1,1'-biphenyl (DPVBi) below:

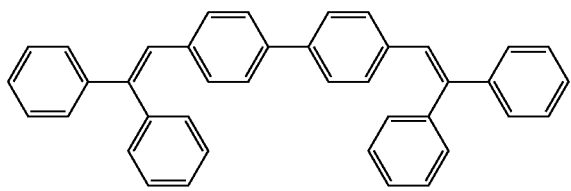 [SMILES: C(=C(c1ccccc1)c1ccccc1)c1ccc(-c2ccc(C=C(c3ccccc3)c3ccccc3)cc2)cc1]

An exemplary triplet-accepting compound has the following formula in the case where q of formula (I) is 0:

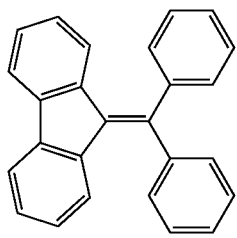 [SMILES: c1ccc(C(=C2c3ccccc3-c3ccccc32)c2ccccc2)cc1]

This compound may optionally be substituted with one or more substituents, such as a substituent $R^5$ as described above, in particular one or more solubilising substituents such as alkyl.

In the case where the light-emitting material is a polymer, the unit of formula (I) may be provided in the form of repeat units in the main chain of the polymer, for example in the form of one of the optionally substituted repeat units illustrated below:

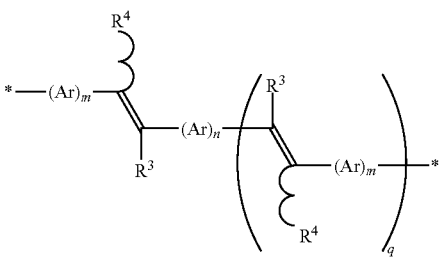

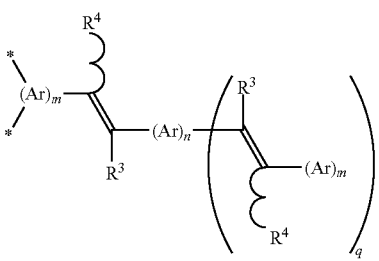

wherein * denotes the linking points for linking the repeat unit into the polymer chain.

Exemplary repeat units include the following:

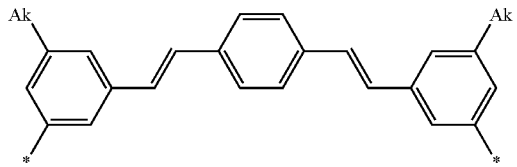

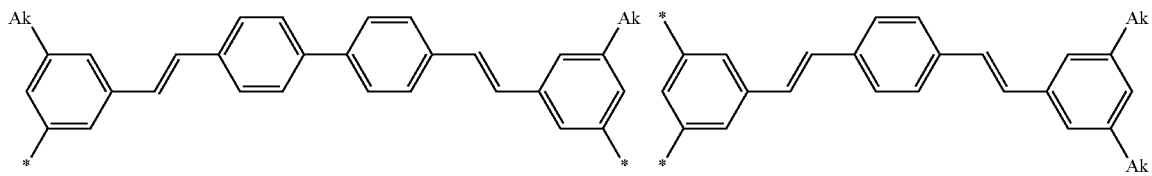

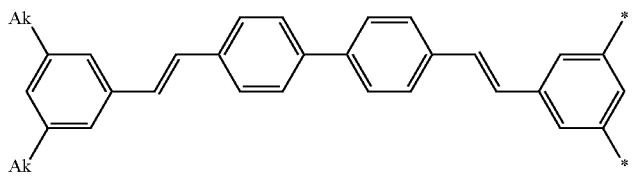

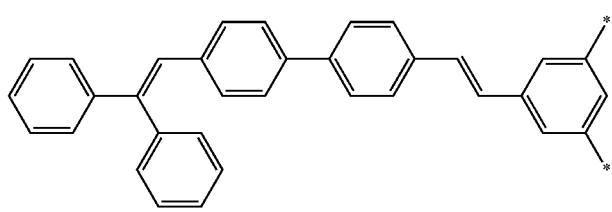

15
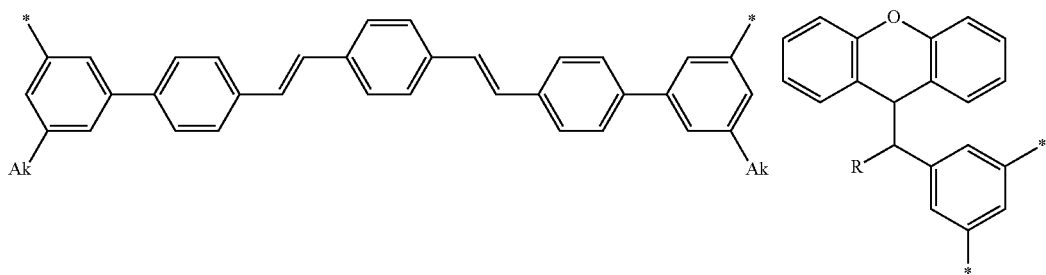
16
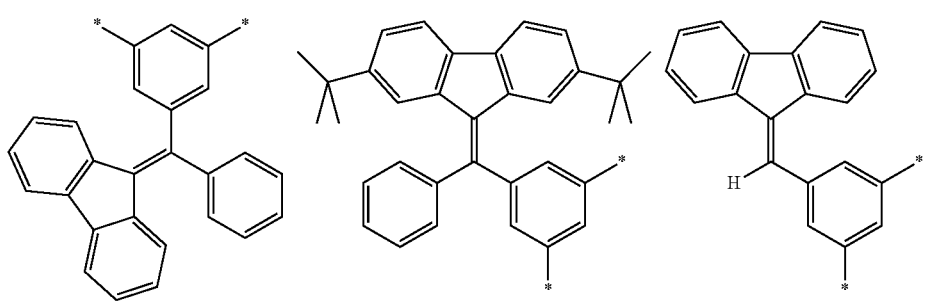
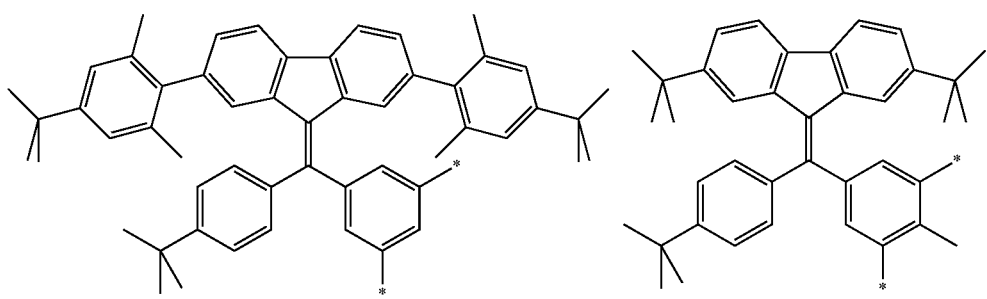
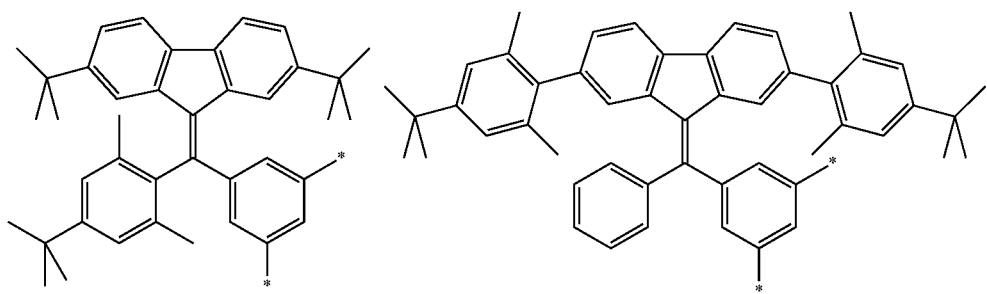
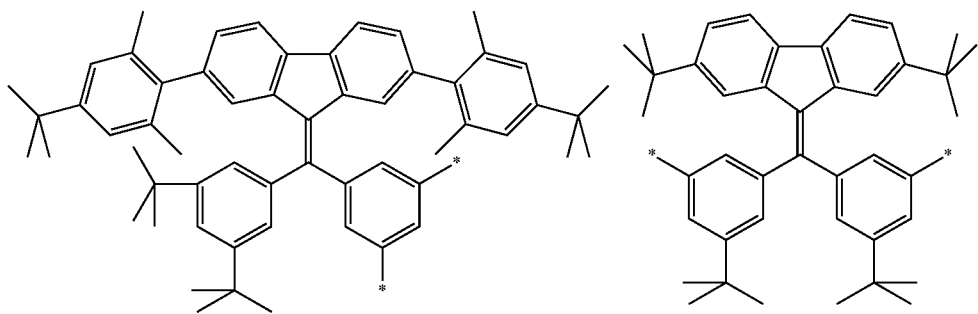

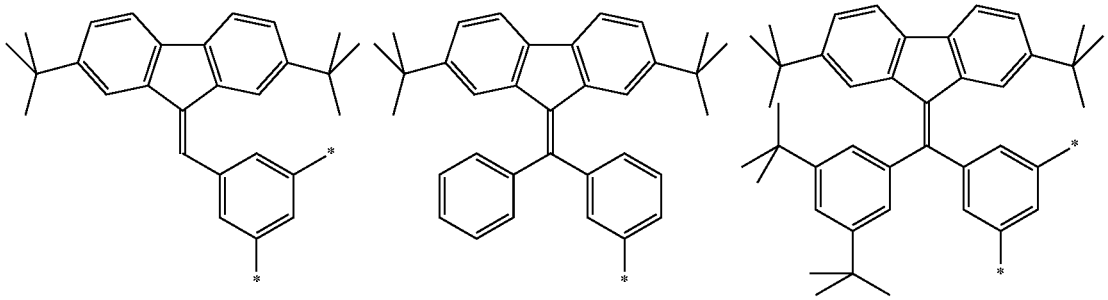

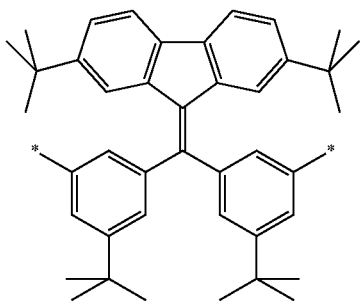

wherein * denotes the linking points for linking the repeat unit into the polymer chain, and Ak is alkyl, in particular branched or straight chain C$_{1-10}$ alkyl. Particularly preferred alkyl groups are n-butyl, t-butyl, n-hexyl and n-octyl. R is H or a substituent, optionally alkyl or optionally substituted aryl or heteroaryl, for example phenyl substituted with one or more alkyl groups.

Additionally or alternatively, the triplet-accepting material may be substituted with one or more aryl or heteroaryl groups, such as one or more phenyl groups. Multiple aryl or heteroaryl groups may be linked to form a straight or branched chain of arylene or heteroarylene groups, for example a dendritic group. Exemplary dendritic groups include the following, each of which may be substituted with one or more substituent groups, for example one or more C$_{1-20}$ alkyl or C$_{1-20}$ alkoxy groups:

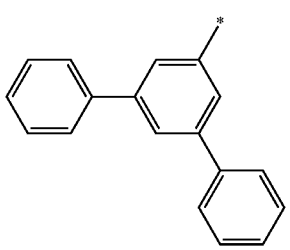

-continued

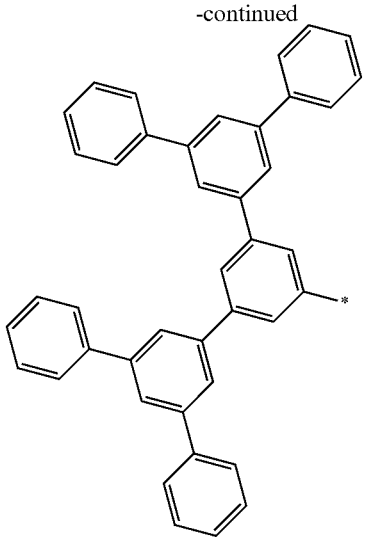

The triplet-accepting unit may be bound into the main chain of a light-emitting polymer by polymerising a monomer comprising the repeat unit illustrated above substituted with a leaving group capable of participating in a metal-catalysed cross-coupling reaction. Exemplary leaving groups include halogen and boronic acid or ester groups for use in Suzuki or Yamamoto polymerisation reactions. These reactions are described in more detail below.

Alternatively, or additionally, in the case where the light-emitting material is a polymer the triplet-accepting unit may be provided in the form of polymer end groups or side-groups pendant from the polymer main chain, for example in the form of an optionally substituted side group or end group as illustrated below:

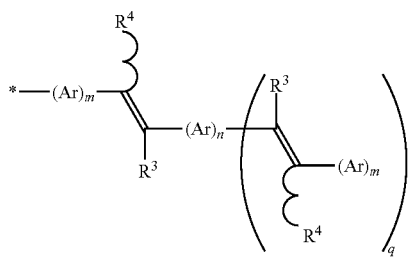

wherein * denotes the linking points for linking the triplet-accepting side-group or end-group to the polymer.

The side-group or end-group may be formed by reacting a compound substituted at * with a suitable leaving group capable of participating in a metal-catalysed cross-coupling reaction, such as a halogen or boronic acid or ester, with a leaving group on the polymer.

Alternatively, a side-group may be incorporated into a light-emitting polymer by providing it as a substituent of a monomer as illustrated below:

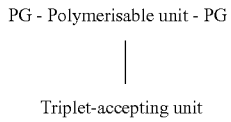

wherein PG represents a polymerisable group such as a leaving group as described above, or a polymerisable double bond. A spacer group, for example an alkylene chain, may separate the polymerisable unit from the triplet-accepting unit. Exemplary polymerisable units include optionally substituted arylenes, for example: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. An exemplary monomer for forming a polymer comprising a triplet-accepting side group has the following formula:

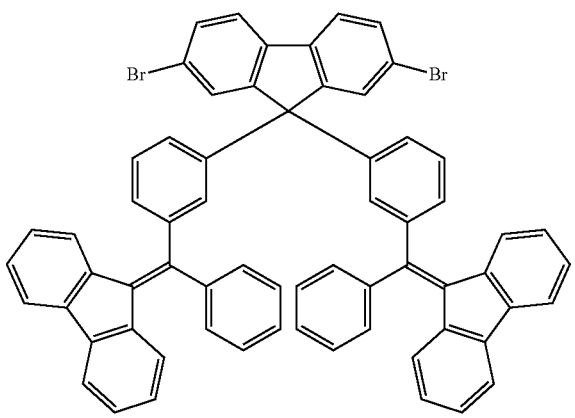 [SMILES: Brc1ccc2c(c1)C(c1cccc(C(=C3c4ccccc4-c4ccccc43)c3ccccc3)c1)(c1cccc(C(=C3c4ccccc4-c4ccccc43)c3ccccc3)c1)c1cc(Br)ccc1-2]

In this example, a fluorene monomer is provided with two triplet accepting units, however it will be appreciated that a fluorene monomer may alternatively be substituted with only one triplet-accepting unit at the fluorene 9-position, the other 9-position being H or a substituent, for example $R^1$ as described below.

An exemplary end-capping unit has the following formula:

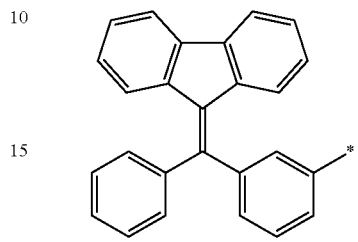

In order to increase the probability of TTA and delayed fluorescence as described above, a plurality of triplet-accepting units may be provided in close proximity. For example, two such units may be provided in an optionally substituted unit having the general formula (III):

TAU-Spacer-TAU        (III)

wherein "TAU" represents a triplet accepting unit of formula (I) and the spacer is a conjugated or non-conjugated spacer group. The spacer group separates the two triplet-accepting TAU groups, and preferably separates their electronic characteristics (for example the HOMO and LUMO). Depending on the precise nature of the conjugation and orbital overlap, Sp could optionally comprise one or more arylene or heteroarylene groups such as substituted phenyl, biphenyl or fluorene. Alternatively, Sp could optionally comprise a non-conjugated linking group such as alkyl, or another molecular link that does not provide a conjugation path between the TAU groups.

The unit of formula (II) may be a separate compound physically mixed with the light-emitting material or it may be bound to the light-emitting material. In the case where the light-emitting material is a polymer, the unit of formula (II) may be bound as a main-chain repeat unit, a side group or an end-group as described above.

Alternatively or additionally, the triplet-accepting unit may be an oligomer or polymer, or a component of an oligomer or polymer, comprising a repeat structure of formula (IIb):

(TAU-Spacer)$_m$        (IIb)

wherein m is at least 2. This oligomer or polymer may be mixed with the light-emitting material or may be provided within the polymer backbone.

Although binding of the triplet-accepting unit to the light-emitting polymer is described above, it will be appreciated that the triplet-accepting unit may be bound to any other component of the composition, where present, in the same way.

The LUMO level of the triplet-accepting unit of formula (I) may be selected so as to provide an electron trap. For example, if the triplet accepting unit is used in combination with an electron transporting material or a light-emitting material comprising electron transporting functionality then the triplet-accepting unit may have a LUMO level that is at least 0.1 eV lower than that of the light-emitting or electron-transporting material. Exemplary electron transporting materials comprise chains of arylene repeat units, for example chains of fluorene repeat units as described in more detail below.

The concentration of the triplet-accepting unit of formula (I) is optionally at least 0.05 mol %, optionally 0.1 mol %, or at least 1 mol %, for example in the range of 0.1-10 mol % or 1-10 mol % relative to the light emitting material. A higher concentration of the triplet-accepting material increases the probability of TTA. In order to increase the probability of TTA, the lifetime of excited state triplets residing on the triplet accepting material is optionally at least 1 microsecond. The lifetime of a triplet exciton is its half-life, which may be measured by flash photolysis to measure monomolecular triplet lifetime as described in Handbook of Photochemistry, 2$^{nd}$ Edition, Steven L Murov, Ian Carmichael and Gordon L Hug and references therein, the contents of which are incorporated herein by reference.

It will be appreciated that, unlike phosphorescent dopants, the triplet-accepting material does not provide an energetically favourable pathway for absorbed triplets to undergo radiative decay, and as a result substantially none of the energy of the triplet exciton absorbed by the triplet-accepting material is lost from the triplet-accepting material in the form of light emission from the triplet-accepting material.

The density of triplet excitons on a light-emitting material, for example on the polymer backbone of a conjugated light-emitting polymer, may be measured using quasi-continuous wave (quasi-cw) excited state absorption as described in more detail below.

Figure 4:
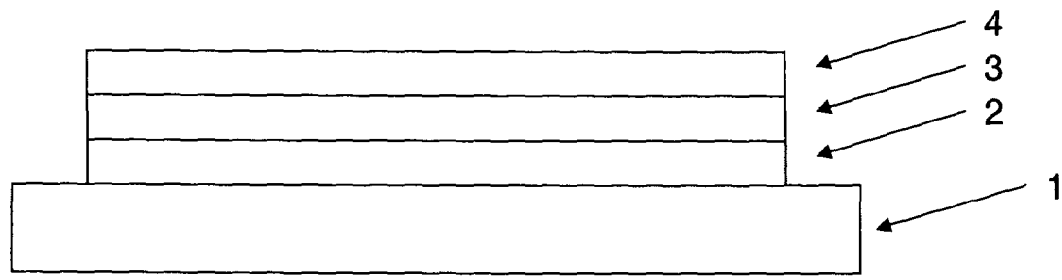
FIG. 4 illustrates an organic light-emitting device according to an embodiment of the invention.

FIG. 4 illustrates the structure of an OLED according to an embodiment of the invention. The OLED comprises a transparent glass or plastic substrate 1, an anode 2, a cathode 4 and a light-emitting layer 3 provided between anode 2 and the cathode 4. Further layers (not shown) may be located between anode 2 and the cathode, such as charge transporting, charge injecting or charge blocking layers.

Organic Semiconducting Material

Suitable organic semiconducting materials, in particular charge transporting and/or light-emitting materials, include small molecule, polymeric and dendrimeric materials, and compositions thereof. Suitable light-emitting polymers for use in layer 3 or charge transporting polymers include poly(arylene vinylenes) such as poly(p-phenylene vinylenes) and polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein.

A suitable light-emitting polymer may be a light-emitting homopolymer comprising light-emitting repeat units, or it may be a copolymer comprising light-emitting repeat units and further repeat units such as hole transporting and/or electron transporting repeat units as disclosed in, for example, WO 00/55927. Each repeat unit may be provided in a main chain or side chain of the polymer.

Polymers for use as charge transporting and/or light-emitting materials in devices according to the present invention preferably comprise a repeat unit selected from arylene repeat units as disclosed in, for example, Adv. Mater. 2000 12(23) 1737-1750 and references therein.

Exemplary first repeat units include: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Particularly preferred polymers comprise optionally substituted, 2,7-linked fluorenes, most preferably repeat units of formula IV:

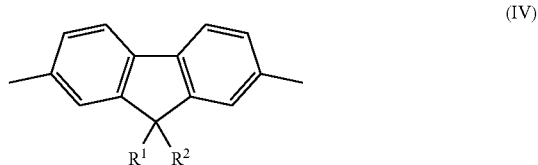

(IV)

wherein $R^1$ and $R^2$ are independently H or a substituent and wherein $R^1$ and $R^2$ may be linked to form a ring. $R^1$ and $R^2$ are preferably selected from the group consisting of hydrogen; optionally substituted alkyl, e.g. $C_{1-20}$ alkyl, wherein one or more non-adjacent C atoms may be replaced with O, S, substituted N, C=O and —COO—; optionally substituted aryl or heteroaryl, e.g. phenyl, or a linear or branched chain of aryl or heteroaryl groups, e.g. phenyl groups, each of which groups may independently be substituted, for example a group of formula $(Ar^3)_v$ as described below; and optionally substituted arylalkyl or heteroarylalkyl. More preferably, at least one of $R^1$ and $R^2$ comprises an optionally substituted $C_4$-$C_{20}$ alkyl or aryl, in particular phenyl, group.

$Ar^3$ in each occurrence is independently selected from aryl or heteroaryl and r is at least 1, optionally 1, 2 or 3

In the case where $R^1$ or $R^2$ comprises one or more aryl or heteroaryl groups, those aryl or heteroaryl groups may be substituted with one or more substituents selected from the group $R^3$ consisting of:

alkyl wherein one or more non-adjacent C atoms may be replaced with O, S, substituted N, C=O and —COO— and one or more H atoms of the alkyl group may be replaced with F or aryl or heteroaryl optionally substituted with one or more groups $R^4$, aryl or heteroaryl optionally substituted with one or more groups $R^4$, $NR^5_2$, $OR^5$, $SR^5$, fluorine, nitro and cyano;

wherein each $R^4$ is independently alkyl in which one or more non-adjacent C atoms may be replaced with O, S, substituted N, C=O and —COO— and one or more H atoms of the alkyl group may be replaced with F, and each $R^5$ is independently selected from the group consisting of alkyl and aryl or heteroaryl optionally substituted with one or more alkyl groups.

In the case where $R^1$ or $R^2$ is aryl or heteroaryl, preferred optional substituents include alkyl groups wherein one or more non-adjacent C atoms may be replaced with O, S, substituted N, C=O and —COO—.

Optional substituents for the fluorene unit, other than substituents $R^1$ and $R^2$, are preferably selected from the group consisting of alkyl wherein one or more non-adjacent C atoms may be replaced with O, S, substituted N, C=O and —COO—, optionally substituted aryl, optionally substituted heteroaryl, alkoxy, alkylthio, fluorine, cyano and arylalkyl. Preferably, the polymer comprises an arylene repeat unit as described above and an arylamine repeat unit, in particular a repeat unit V:

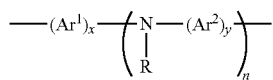
(V)

wherein $Ar^1$ and $Ar^2$ are optionally substituted aryl or heteroaryl groups, n is greater than or equal to 1, preferably 1 or 2, R is H or a substituent, preferably a substituent; and x and y are each independently 1, 2 or 3. R may be —$(Ar^3)_v$, wherein $Ar^3$ in each occurrence is independently selected from aryl or heteroaryl and v is at least 1, optionally 1, 2 or 3. In the case where v is greater than 1, —$(Ar^3)_v$ may form a straight or branched chain of $Ar^3$ groups. R is preferably alkyl or aryl or heteroaryl, most preferably aryl or heteroaryl. Any of the aryl or heteroaryl groups in the unit of formula 1, including the case where R comprises one or more aryl or heteroaryl groups, may be substituted. Preferred substituents are selected from alkyl wherein one or more non-adjacent C atoms may be replaced with O, S, substituted N, C=O and —COO—, optionally substituted aryl, optionally substituted heteroaryl, alkoxy, alkylthio, fluorine, cyano and arylalkyl. Preferred substituents include alkyl and alkoxy groups. Any of the aryl or heteroaryl groups in the repeat unit of Formula 1 may be linked by a direct bond or a divalent linking atom or group. Preferred divalent linking atoms and groups include O, S; substituted N; and substituted C.

$Ar^1$, $Ar^2$ and $Ar^3$ in each occurrence are preferably phenyl, and each phenyl which may independently be substituted with one or more substituents as described above. Exemplary substituents are alkyl, such as $C_{1-20}$ alkyl.

The repeat unit of formula (V) may have the following formula, wherein x and y are both 1:

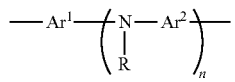

Particularly preferred units satisfying Formula 1 include units of Formulae 1-3:

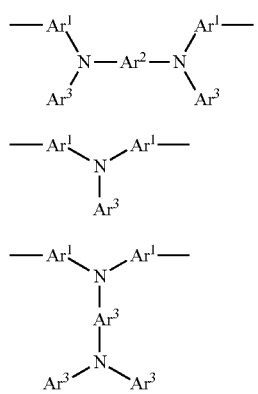

wherein $Ar^1$ and $Ar^2$ are as defined above; and $Ar^3$ is optionally substituted aryl or heteroaryl. Where present, preferred substituents for $Ar^3$ include alkyl and alkoxy groups.

Polymers comprising repeat units of formula (V) may be used as light-emitting materials in layer 3 of the OLED, or as hole transporting materials used in layer 3 or in a hole transporting layer of the OLED.

The polymer may comprise one, two or more different repeat units of formula (V). For example, the polymer may comprise one repeat unit of formula (V) to provide hole transport and another repeat unit of formula (V) to provide light-emission.

The arylamine repeat units are preferably present in an amount up to 30 mol %, preferably up to 20 mol %. These percentages apply to the total number of arylamine units present in the polymer in the case where more than one type of repeat unit of formula V is used.

The polymer may comprise heteroarylene repeat units for charge transport or emission.

Binding the triplet-accepting unit to a charge transporting or light-emitting material may result in more efficient triplet acceptance as compared to mixing of a triplet-accepting material with the charge transporting or light-emitting material because this binding may provide intramolecular triplet acceptance pathways unavailable to a corresponding mixed system. In the case where a charge transporting and/or light-emitting polymer is used, the triplet-accepting unit may be bound to any repeat unit of the polymer. For example, in the case of a light emitting polymer the triplet-accepting unit may be bound to a light-emitting repeat unit of the polymer and/or to any other repeat unit of the polymer that may be present, for example an electron transporting repeat unit and/or a hole transporting repeat unit.

Moreover, binding may be beneficial for processing reasons. For example, if the compound of formula (I) has low solubility then binding it to a soluble charge transporting or light-emitting material, in particular a soluble charge transporting or light-emitting polymer, allows the triplet-accepting unit to be carried in solution by the charge transporting or light-emitting material, enabling device fabrication using solution processing techniques. Furthermore, if the triplet-accepting unit is a relatively volatile material then the risk of evaporation of the triplet accepting material during device fabrication is eliminated. This is a particular issue in the case of OLEDs formed using solution processing methods because charge transporting and light-emitting layers formed by deposition of a solution are typically heated as part of the device fabrication process (for example, to evaporate the solvent), which increases the likelihood of evaporation of volatile triplet-accepting units. Finally, binding the triplet accepting unit to the charge transporting or light-emitting material may prevent phase separation effects in solution-processed devices that may be detrimental to device performance.

Where the light-emitting material is a conjugated polymer comprising light-emitting repeat units and further repeat units, for example light-emitting amine repeat units of formula (V) and fluorene repeat units of formula (IV), conjugation of the triplet-accepting unit into the polymer main chain (for example by conjugation with fluorene repeat units) may reduce the $T_1$ energy level of the triplet-accepting unit, thus increasing the energetic favourability of triplet exciton transfer from the emitter unit to the triplet-accepting unit. This reduction in $T_1$ energy level of the triplet-accepting unit may also enable use of the triplet-accepting unit with light-emitting materials with $T_1$ levels that are too low for use with a triplet-accepting unit that is not conjugated in this way.

Preferred methods for preparation of conjugated charge transporting and light-emitting polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable □-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

Light-emitting layer 3 may consist of the light-emitting polymer and the triplet accepting unit alone, alone or may comprise these materials in combination with one or more further materials. In particular, the light-emitting polymer may be blended with hole and/or electron transporting materials or alternatively may be covalently bound to hole and/or electron transporting materials as disclosed in for example, WO 99/48160.

Light-emitting copolymers may comprise a light-emitting region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality—for example, an amine unit as described above may provide both hole transport and light-emission functionality. A light-emitting copolymer comprising light-emitting repeat units and one or both of a hole transporting repeat units and electron transporting repeat units may provide said units in a polymer main-chain, as disclosed in U.S. Pat. No. 6,353,083, or in polymer side-groups pendant from the polymer backbone.

The light-emitting polymer may emit light of any colour provided that its $S_1$ and $T_1$ energy levels relative to the triplet-accepting unit are as described above, however the light-emitting polymer is preferably a blue light-emitting polymer, in particular a material having photoluminescent light emission with a peak wavelength in the range of from 400 to 500 nm, preferably 430 to 500 nm.

Light-emitting layer 3 may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned light-emitting layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

B. Light-Emission

In the case where a unit of formula (I) is used as a light-emitting material, the unit may be used in combination with a host material, such as a polymeric host material, from which it receives singlet excitons, wherein the $S_1$ level of the unit of formula (I) is lower than, or at least no higher than, that of the host.

The unit of formula (I) may be a compound that is physically mixed with, and not chemically bound to, its host material. Alternatively, the unit of formula (I) may be chemically bound to its host material. In the case of a polymeric host material the unit of formula (I) may be provided as a repeat unit in the polymer main chain or bound to the polymer as a side group or end group. Suitable light-emitting compounds, repeat units, side groups and end groups of formula (I) are as described above with respect to triplet-accepting materials.

A suitable host material in this case includes fluorene homopolymer or a copolymer comprising fluorene units and one or more co-repeat units having an $S_1$ level higher than that of the unit of formula (I).

Exemplary materials, processes and device architectures of the OLED are described in more detail below. It will be appreciated that these materials, processes and device architectures are applicable to any OLED comprising a unit of formula (I), regardless of whether that unit is functioning as an emitter unit or a substantially non-emissive triplet-accepting unit.

Hole Injection Layers

A conductive hole injection layer, which may be formed from a conductive organic or inorganic material, may be provided between the anode 2 and the light-emitting layer 3 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Charge Transporting Layers

A hole transporting layer may be provided between the anode and the light-emitting layer. Likewise, an electron transporting layer may be provided between the cathode and the light-emitting layer.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

If present, a hole transporting layer located between anode 2 and light-emitting layer 3 preferably has a HOMO level of less than or equal to 5.5 eV, more preferably around 4.8-5.5 eV. HOMO levels may be measured by cyclic voltammetry, for example.

If present, an electron transporting layer located between light-emitting layer 3 and cathode 4 preferably has a LUMO level of around 3-3.5 eV. For example, a layer of a silicon monoxide or silicon dioxide or other thin dielectric layer having thickness in the range of 0.2-2 nm is provided between light-emitting layer 3 and layer 4.

Polymers for use as charge transporting materials may comprise arylene units, such as fluorene units of formula (IV) and other units described above.

A hole-transporting polymer may comprise arylamine repeat units, in particular repeat units of formula (V), such as repeat units of formulae 1-3, described above. This polymer may be a homopolymer or it may be a copolymer comprising arylene repeat units in an amount up to 95 mol %, preferably up to 70 mol %. These percentages apply to the total number of arylamine units present in the polymer in the case where more than one type of repeat unit of formula (V) is used.

Charge transporting units may be provided in a polymer main-chain or polymer side-chain.

Where present, a charge transporting layer may comprise a charge transporting material and a triplet-absorbing material in an arrangement analogous to that described above, in which case the light-emitting layer 3 may or may not comprise a triplet accepting unit.

Cathode

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminium. Alternatively, it may comprise a plurality of metals, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode will comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

OLEDs tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to preventingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Light-emitting layer 3 may be deposited by any process, including vacuum evaporation and deposition from a solution in a solvent. In the case where the light emitting layer comprises a polyarylene, such as a polyfluorene, suitable solvents for solution deposition include mono- or poly-alkylbenzenes such as toluene and xylene. Particularly preferred solution deposition techniques including printing and coating techniques, preferably spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

If multiple layers of an OLED are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

MATERIAL EXAMPLE

A compound of formula (I) was prepared according to the following synthetic method:

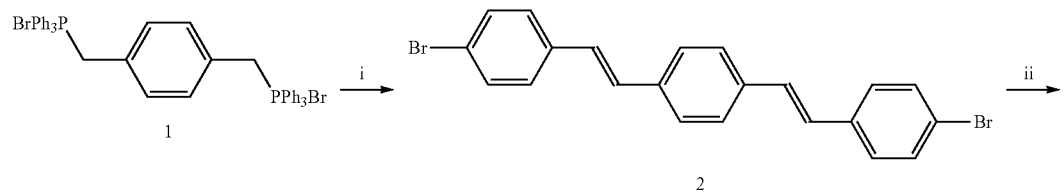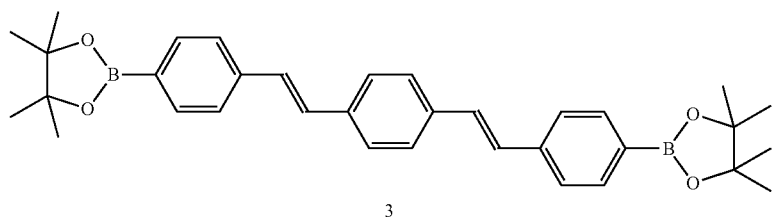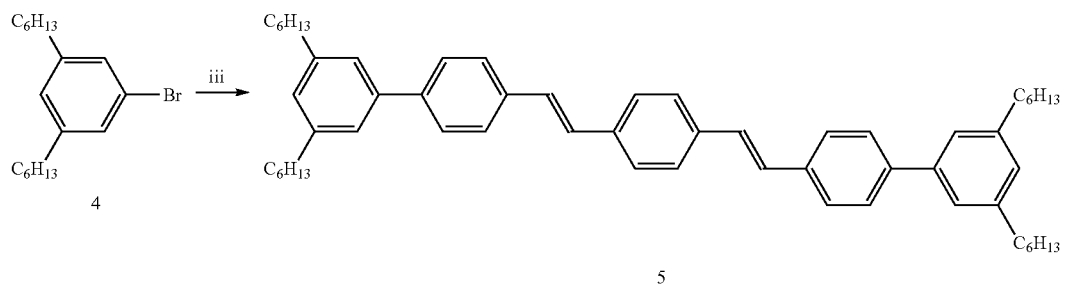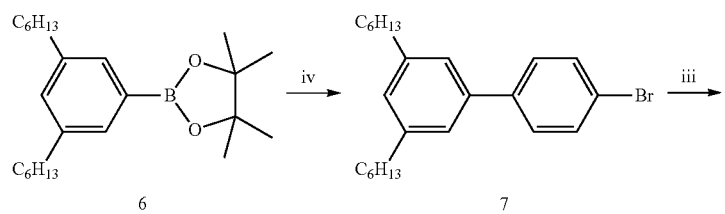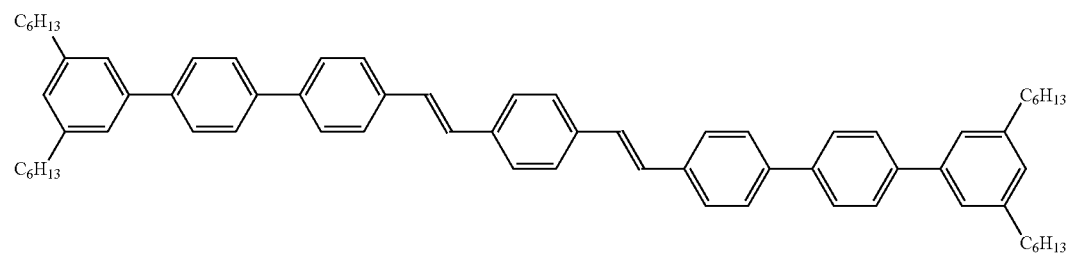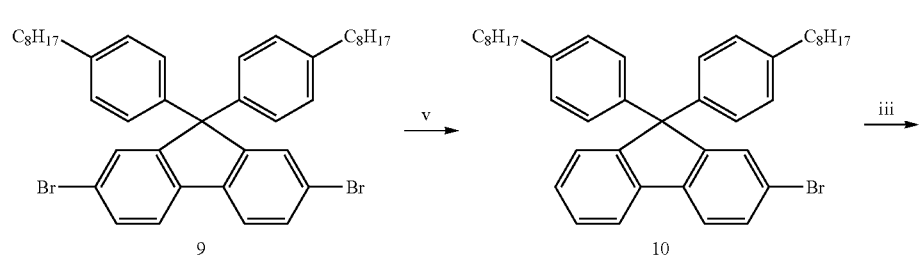

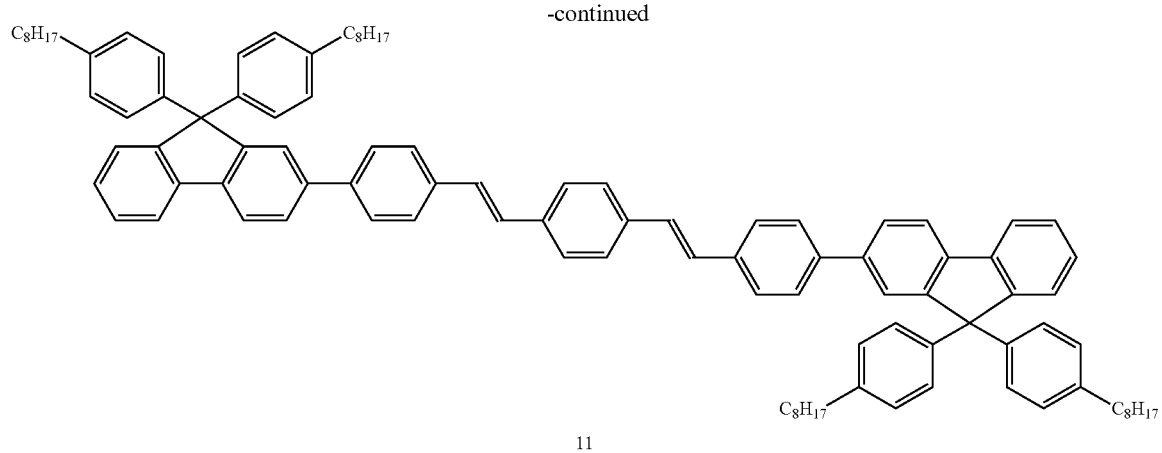

11 i. 4-bromobenzaldehyde, NaO'Bu, THF, ii. BuLi, IPB, THF, iii. 3, Pd(PPh₃)₂Cl₂, Et₄NOH, toluene, iv. 1-bromo-4-iodobenzene, Pd(PPh₃)₄, Ag₂CO₃, THF, v. BuLi, H₂O, THF Triplet quenching material 12, reactive compound 13 for forming an triplet-quenching end group or side group of a polymer and monomers 14, 16 and 18 for forming triplet-quenching repeat units were prepared according to the following methods:

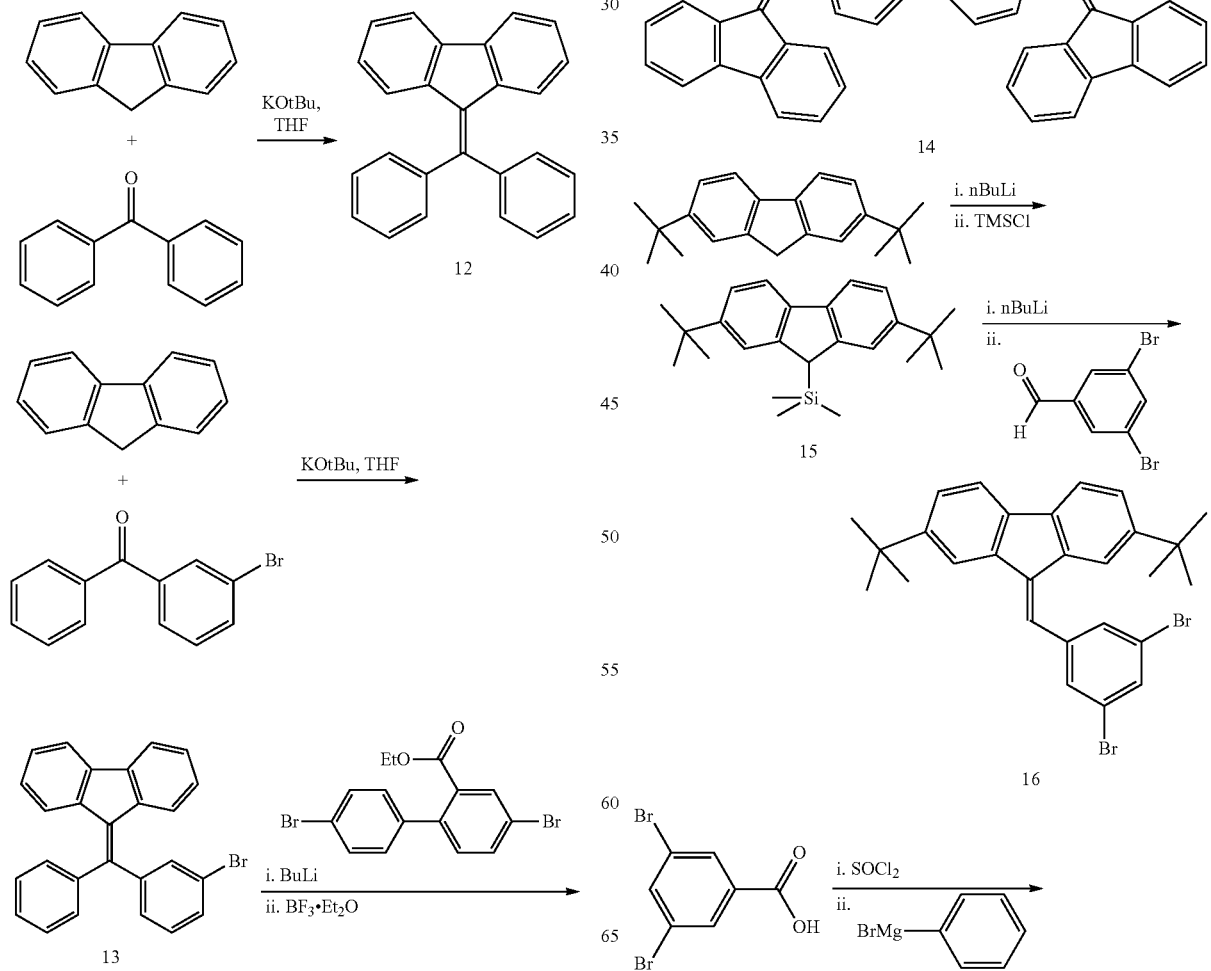

-continued

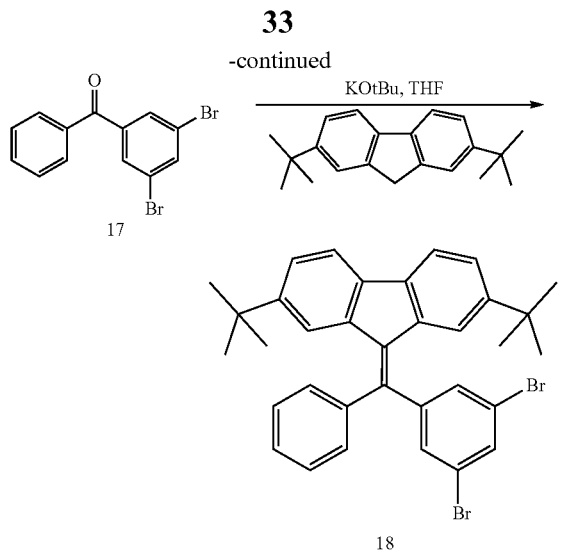

Compound 2
To an ice-cooled solution of p-xylylenebis(triphenylphosphonium bromide) (81.3 g, 103 mmol) and p-bromobenzaldehyde (38.3 g, 207 mmol) in anhydrous tetrahydrofuran (1000 ml) was added sodium tert-butoxide (22.0 g, 229 mmol) and the reaction mixture was allowed to warm to room temperature with stirring over night. After aqueous work-up and treatment with iodine in refluxing toluene, the title compound was isolated as a yellow solid (20.3 g, 46 mmol).

Compound 3
To a solution of compound 2 (4.40 g, 10 mmol) in anhydrous tetrahydrofuran (200 ml) cooled to −78° C. was added n-butyl lithium (2.5M in hexanes, 12 ml, 30 mmol) and subsequently isopropoxyboronic acid pinacol ester (5.60 g, 30 mmol). The reaction mixture was allowed to warm to room temperature and quenched with acid. Column chromatography (silica, toluene) afforded the title compound as a yellow solid (2.95 g, 5.5 mmol).

Compound 5
A solution of compound 3 (1.21 g, 2.3 mmol), compound 4 (1.80 g, 5.5 mmol) and bis(triphenylphosphine)palladium(II) dichloride (0.088 g, 0.13 mmol) in toluene (75 ml) and tetraethyl ammonium hydroxide (20 wt % in water, 15 ml, 20 mmol) was stirred at reflux over night. After an aqueous work-up, column chromatography (silica, hexane/toluene) and recrystallisation afforded the title compound as a yellow solid (0.44 g, 0.6 mmol).

Compound 7
A solution of compound 6 (10.0 g, 27 mmol) and 1-bromo-4-iodobenzene (11.4 g, 40 mmol), silver carbonate (14.8 g, 54 mmol) and tetrakis(triphenylphosphine)palladium(0) (3.11 g, 2.7 mmol) in anhydrous tetrahydrofuran (200 ml) was refluxed over night. Column chromatography (silica, hexane) afforded the title compound as a colourless oil (4.07 g, 10 mmol).

Compound 8
According to the procedure described for compound 5 using compound 3 (2.47 g, 4.6 mmol) and compound 7 (4.05 g, 10 mmol), the title compound was obtained as a yellow solid (2.0 g, 2.2 mmol).

Compound 10
To a solution of compound 9 (20.0 g, 29 mmol) in anhydrous tetrahydrofuran (300 ml) cooled to −78° C. was added n-butyl lithium (2.5M in hexanes, 11.5 ml, 29 mmol) and subsequently water (10 ml, 555 mmol). The reaction mixture was allowed to warm to room temperature. Column chromatography (silica, hexane/toluene) afforded the title compound as a colourless oil (6.0 g, 9.7 mmol).

Compound 11
According to the procedure described for compound 5 using compound 3 (1.84 g, 3.4 mmol) and compound 10 (4.67 g, 7.1 mmol), the title compound was obtained as a yellow solid (0.84 g, 0.6 mmol).

Compound 12
Dry tetrahydrofuran (500 ml) was added to a mixture of fluorene (10.00 g, 60.16 mmoles) and potassium tert-butoxide (7.43 g, 66.18 mmoles) under nitrogen and stirred at room temperature for 5 minutes. Benzophenone (10.96 g, 60.16 mmoles) was then added as a solid and the reaction mixture was stirred for a further 20 hours under nitrogen at room temperature. Aqueous ammonium chloride (sat., 200 ml) was then added and stirred until the colour had faded. Diethyl ether (100 ml) was added and the aqueous layer separated and extracted with diethyl ether (2×100 ml). The combined organic layers were washed with water (3×200 ml), dried over anhydrous magnesium sulfate and evaporated. The crude product (16.0 g) was recrystallised twice from dichloromethane:hexane (100:200 ml) and then from dichloromethane:acetonitrile (100:200 ml) and then dried under vacuum to give white crystals of 9-(diphenylmethylene)-9H-fluorene (7.34 g).

Compound 13
According to the procedure described for compound 12 using fluorene (31.83 g, 191.5 mmol) and 3-bromobenzophenone (50.00 g, 191.5 mmol), then following recrystallisation from dichloromethane:hexane the title compound was obtained as an off-white crystalline solid (62.11 g, 162 mmol).

Compound 14
A solution of compound 13 (30.00 g, 73.29 mmoles) in dry tetrahydrofuran (200 ml) under nitrogen was cooled to below −70° C. in an acetone/dry ice bath and then n-butyl lithium (2.5M in hexanes, 28.0 ml, 70.1 mmoles) was added dropwise. The reaction mixture was stirred below −70° C. for 90 minutes and then a solution of ethyl 4,4'-dibromobiphenyl-2-carboxylate (11.79 g, 31.9 mmoles) in dry tetrahydrofuran (40 ml) was added dropwise and the reaction mixture was stirred for a further 40 hours while allowing to warm to room temperature. Aqueous ammonium chloride (sat., 50 ml) was then added and stirred for 20 minutes. Diethyl ether (200 ml) was then added and the aqueous layer was separated and extracted with diethyl ether (2×50 ml). The combined organic layers were washed with water (3×100 ml), dried over anhydrous magnesium sulphate and then evaporated. The crude intermediate was dissolved in dry dichloromethane (200 ml) under nitrogen and cooled in a sodium chloride/ice bath. Boron trifluoride etherate (38 ml) was added dropwise and the dark solution was stirred overnight, allowing to warm to room temperature. The reaction mixture was then poured onto ice/water (500 ml) and aqueous potassium phosphate (20 g in 200 ml) was added and stirred for 1 hour. The aqueous layer was separated and extracted with dichloromethane (2×50 ml) and the combined organic layers were washed with water (2×100 ml), dried over anhydrous magnesium sulphate and then evaporated to give an orange oil. This was triturated twice with hexane and then recrystallised from toluene:acetonitrile to give the title compound (20.5 g, 20.9 mmoles).

Compound 15
n-Butyl lithium (95 ml, 2.5 M in hexanes, 238 mmoles) was added dropwise to a solution of 2,7-di-tert-butylfluorene (66.3 g, 238 mmoles) in dry diethyl ether (1.4 L) under nitrogen in an ice-bath and then stirred for 20 minutes. Chlorotrimethylsilane (40 ml, excess) was added and stirred for 6 hours, with gradual warming to room temperature. Water (500 ml) was added and the organic layer was separated, washed with water (3×100 ml), dried over anhydrous magnesium sulphate and evaporated to give an orange solid. Recrystallisation from hot hexane gave the title compound (60.7 g, 73%)

Compound 16 n-Butyl lithium (7.4 ml, 2.5 M in hexanes, 18 mmoles) was added slowly to a solution of 2,7-di-tert-butyl-9-trimethylsilylfluorene (7.11 g, 20.2 mmoles) in dry diethyl ether (100 ml) at 0° C. under nitrogen and stirred for 15 minutes. Dibromobenzaldehyde (4.87 g, 18.4 mmoles) was added and the reaction was stirred at room temperature for 2 hours. Water (50 ml) was added and the organic layer was separated, washed with water (3×30 ml), dried over anhydrous magnesium sulphate and evaporated to give an orange oil. Recrystallisation from hexane, acetonitrile and propan-2-ol gave the title compound.

Compound 17

Thionyl chloride (100 ml) was added to 3,5-dibromobenzoic acid (50.0 g, 178 mmoles) and heated at reflux for 6 hours. The excess thionyl chloride was then removed by distillation and the remaining brown solid was dissolved in dry tetrahydrofuran (1 L) and cooled to below −70° C. under nitrogen in an acetone/dry ice bath. Phenyl magnesium bromide solution (179 ml, 1M in tetrahydrofuran, 179 mmoles) was added dropwise to the cold reaction mixture and the temperature was then allowed to rise to room temperature while stirring for 4 hours. Water (200 ml) was cautiously added followed by diethyl ether (200 ml). The aqueous layer was separated and extracted with diether ether (2×50 ml) and then combined organic layers were then washed with water (3×100 ml), dried over magnesium sulphate and evaporated. Trituration with methanol released a white solid which, after recrystallisation from hexane, gave the title compound (23.66 g).

Compound 18

According to the procedure described for compound 12 using 2,7-di-tert-butylfluorene (19.37 g, 69.6 mmol) and 3,5-dibromobenzophenone (23.66 g, 69.6 mmol), then following recrystallisation from hexane, column chromatography on silica (eluting with 5% dichloromethane:hexane) and further recrystallisation from dichloromethane:methanol, the title compound was obtained as a yellow solid (0.90 g).

Compound 19

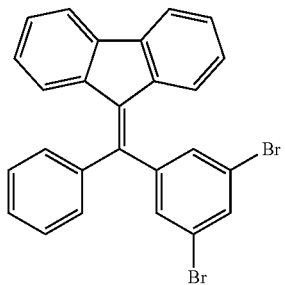

Compound 19 was prepared following the method illustrated above in relation to Compound 18 by reaction of intermediate 17 illustrated above as set out below.

Potassium tert-butoxide (39.16 g, 342 mmoles) was added to a solution of fluorene (58.0 g, 342 mmoles) in dry tetrahydrofuran (400 ml) under nitrogen and stirred at room temperature until fully dissolved. The reaction mixture was then cooled down to −75° C. and a solution of 3,5-dibromobenzophenone (116.3 g, 342 mmoles) in dry tetrahydrofuran (350 ml) was added dropwise, maintaining the temperature below −70° C. and then stirred overnight while allowing to warm to room temperature. The reaction was then cooled and aqueous ammonium chloride (sat., 250 ml) was added and stirred at 0° C. for 20 minutes and then the tetrahydrofuran was removed under vacuum. Water (1 L) was added and extracted with dichloromethane (3×250 ml) and the combined organic fractions were washed with water (3×300 ml), dried over magnesium sulfate and evaporated to give a brown oil. Purification by column chromatography (hexane+increasing dichloromethane) followed by trituration with hexane and recrystallisation from dichloromethane:methanol gave the desired product as a pale yellow solid (38.2 g).

Device Example 1

Triplet Acceptance

A device having the following structure was formed:
ITO/HIL/HTL/EL/MF/Al
wherein ITO represents an indium-tin oxide anode; HIL is a hole-injection layer formed from a hole injection material available from Plextronics Inc.; HTL is a hole transport layer of a polymer comprising fluorene repeat units of formula (IV) and amine repeat units of formula (V); EL is an light-emitting layer comprising fluorene repeat units of formula (IV) and amine repeat units of formula (V) blended with 0.25 mol % of DPVBi; MF is a metal fluoride; and the bilayer of MF/Al forms a cathode for the device.

Device Examples 2-4

Triplet Acceptance

Three further devices were prepared as above, except that DPVBi was provided in concentrations of 0.5, 1 and 3 mol % (devices 2, 3 and 4 respectively).

Figure 5:
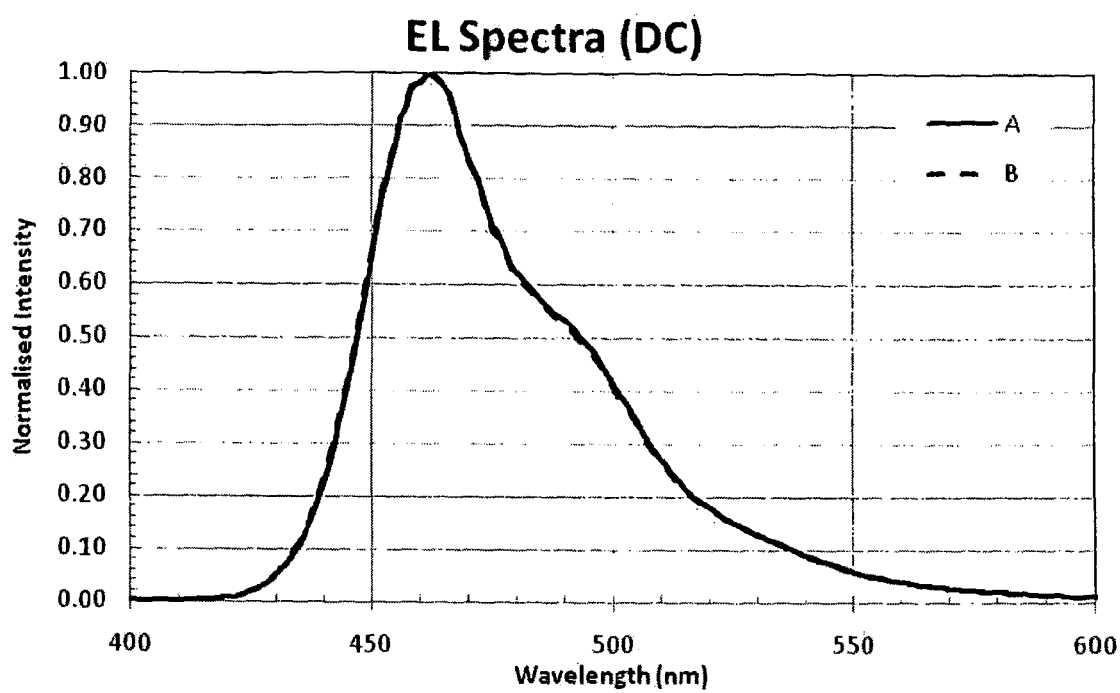
FIG. 5 illustrates the electroluminescent spectrum of an exemplary OLED of the invention compared to the electroluminescent spectrum of a comparative device.

As shown in FIG. 5 device 3 has an electroluminescent spectrum (B) that is virtually identical to that of a comparative device (A) in which no triplet-accepting compound is present, indicating that the $S_1$ energy level of the triplet-accepting compound is higher than that of the light-emitting unit of the polymer.

Figure 6:
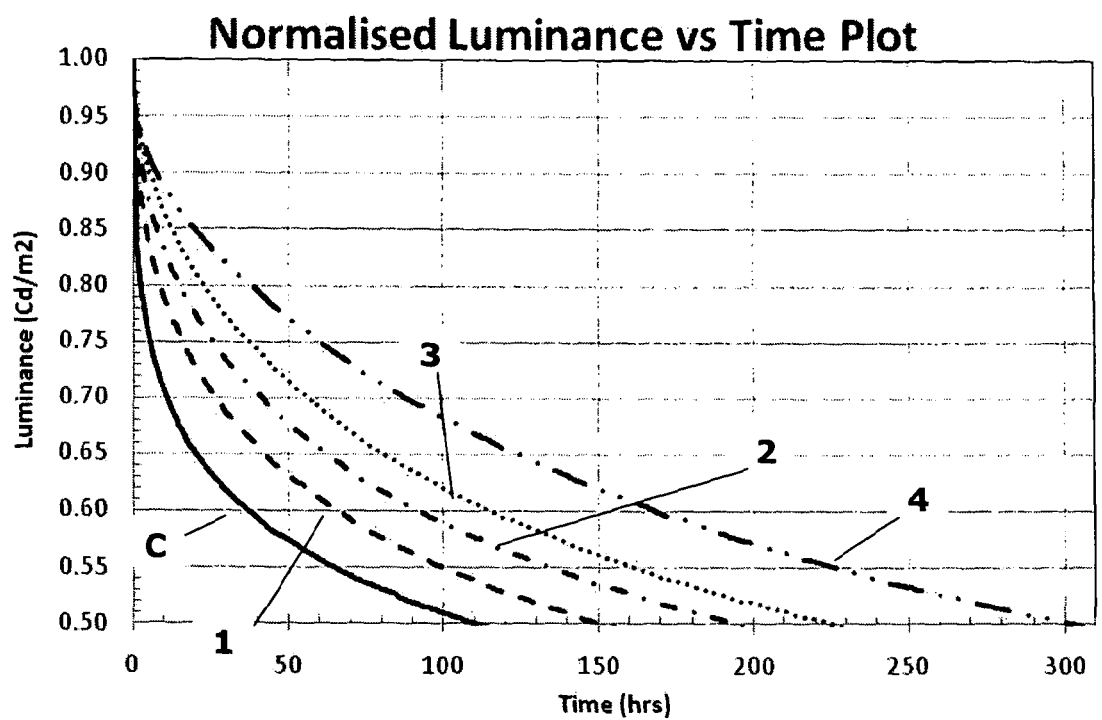
FIG. 6 illustrates the lifetime of 4 exemplary OLEDs of the invention compared to a comparative device.

As shown in FIG. 6, the $T_{90}$ lifetime (that is, the time taken for the device brightness to fall to 90% of its original brightness at constant current) is longer for the exemplary devices 1-4 than for the comparative device (C) in all cases, and the lifetime decay curve is considerably flatter as compared to the curve of the comparative device (C), in which brightness falls sharply at first before flattening out.

Figure 7:
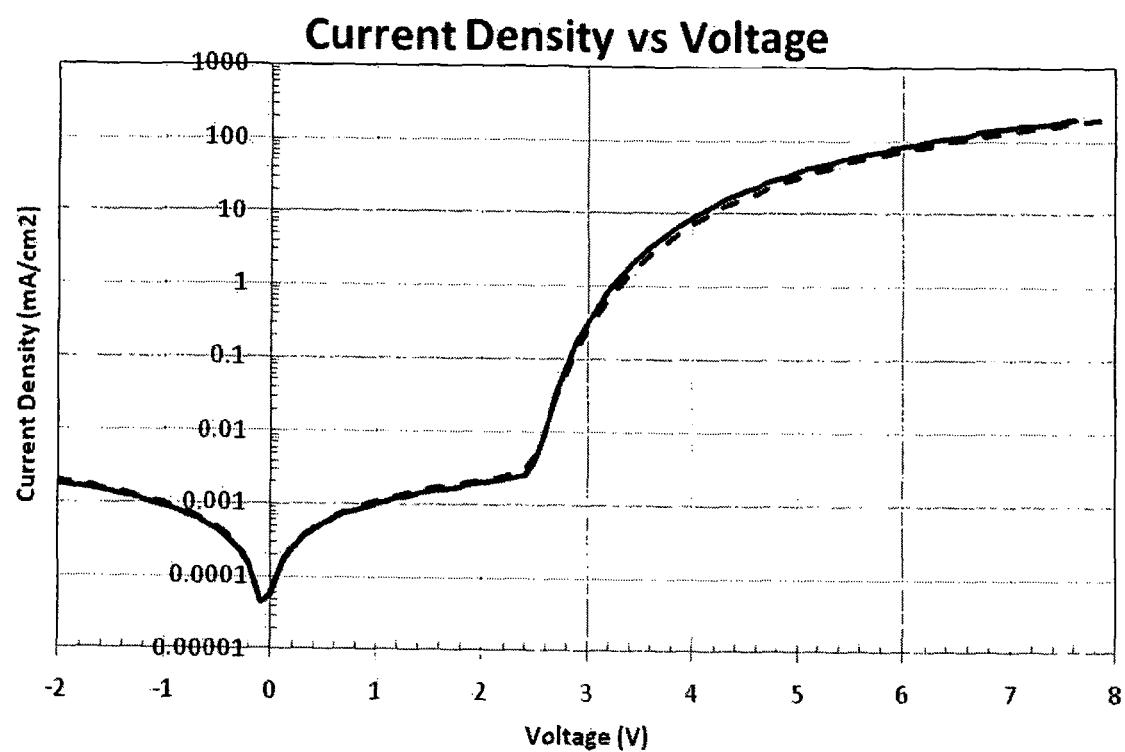
FIG. 7 illustrates the current density vs. voltage of an exemplary OLED of the invention compared to a comparative device.

FIG. 7 illustrates that current density against voltage characteristics for device 3 (dotted line) and the comparative device (solid line) are virtually identical.

Figure 8:
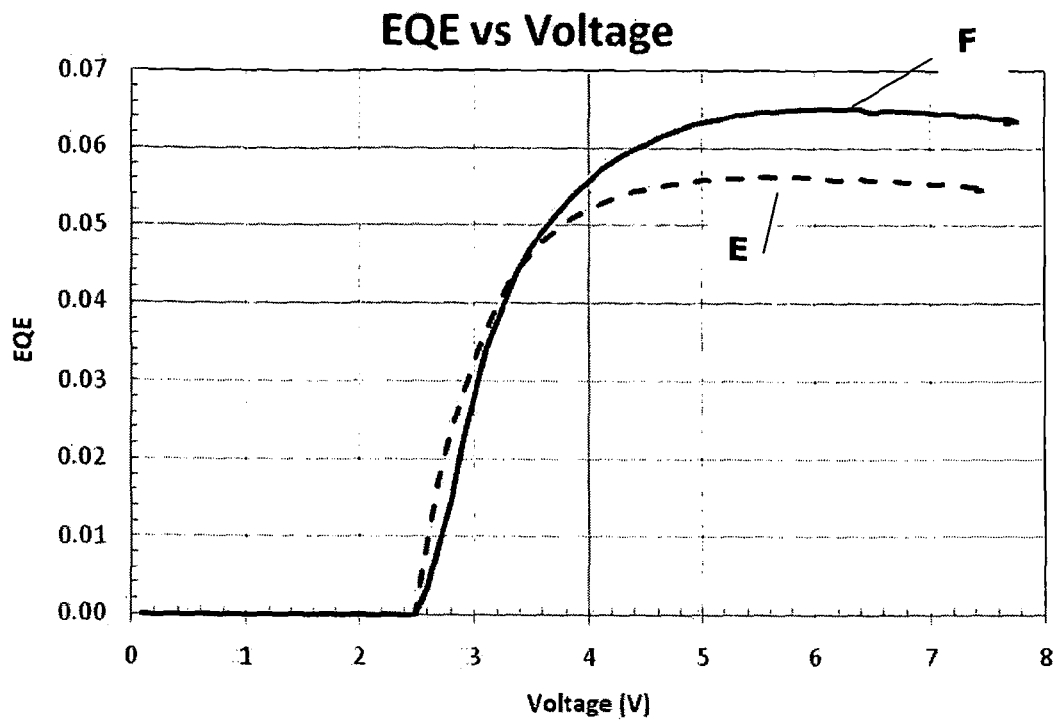
FIG. 8 illustrates the external quantum efficiency vs. voltage of an exemplary OLED of the invention compared to a comparative device.

FIG. 8 illustrates a drop in external quantum efficiency in comparing device 3 (dotted line, E) with the comparative device (solid line, F). This is to be expected in the present case wherein triplets are quenched resulting in no triplet-triplet annihilation of triplets residing on the light-emitting polymer, however efficiency may be restored by causing triplet-triplet annihilation as described hereinbefore.

Device Example 5

A device was formed as per Device Example 1, wherein HTL comprises the 50:50 mol copolymer F8-TFB (poly-(9, 9-dioctylfluorene-N-(4-(2-butyl)phenyl)-diphenylamine)) and EL comprises the 95:5 mol copolymer F8-PFB (poly-(9, 9'-dioctylfluorene-co-bis-N,N'-(4-butylphenyl)-bis-N,N'-phenyl-1,4-phenylenediamine)) blended (1% mol ratio) with a triplet quenching additive DPVBi (4,4'-bis(2,2' diphenyl vinyl)-1,1'-biphenyl).

DPVBi has a triplet energy in the red-green portion of the spectrum (see Chen, P. et al. White organic light-emitting devices with a bipolar transport layer between blue fluorescent and orange phosphorescent emitting layers. *Appl. Phys. Lett.* 91, 023505-3 (2007); Schwartz, G., Fehse, K., Pfeiffer, M., Walzer, K. & Leo, K. Highly efficient white organic light emitting diodes comprising an interlayer to separate fluorescent and phosphorescent regions. *Applied Physics Letters* 89, 083509 (2006); and Romanovskii, Y. V. et al. Phosphorescence of pi-conjugated oligomers and polymers. *Phys. Rev. Lett.* 84, 1027-1030 (2000).

DPVBi also has a high singlet energy (3.2 eV) compared to the luminescent polymer so this molecule will accept the polymer triplets without affecting the emissive singlet states, this is confirmed by the observation that the incorporation of this small molecule into the polymer does not affect either the intensity or spectrum of the device photoluminescence.

The dynamics of the singlet and triplet excitons were studied using time resolved electroluminescence as well as quasi-cw and time resolved excited state absorption. The excited state absorption techniques have been described elsewhere (King, S., Rothe, C. & Monkman, A. Triplet build in and decay of isolated polyspirobifluorene chains in dilute solution. *J. Chem. Phys.* 121, 10803-10808 (2004), and Dhoot, A. S., Ginger, D. S., Beljonne, D., Shuai, Z. & Greenham, N. C. Triplet formation and decay in conjugated polymer devices. *Chemical Physics Letters* 360, 195-201 (2002)) and the triplet state of polyfluorenes has been well characterised with these techniques with a strong excited state absorption feature peaking at 780 nm attributed to the triplet state (King, S., Rothe, C. & Monkman, A. Triplet build in and decay of isolated polyspirobifluorene chains in dilute solution. *J. Chem. Phys.* 121, 10803-10808 (2004) and Rothe, C., King, S. M., Dias, F. & Monkman, A. P. Triplet exciton state and

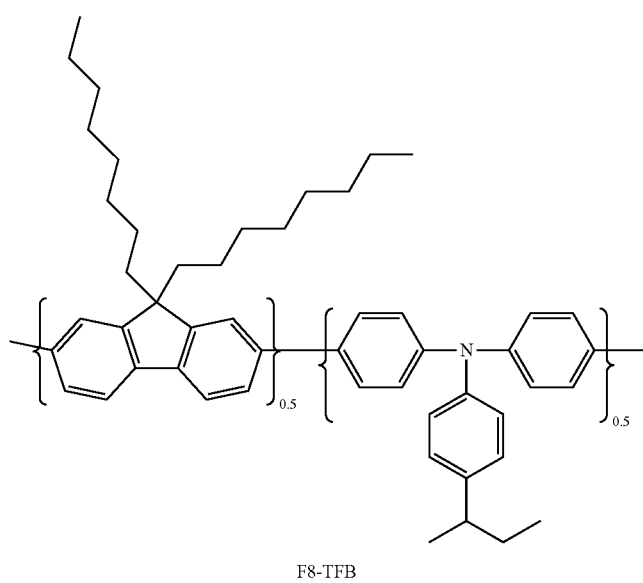

F8-TFB (1)

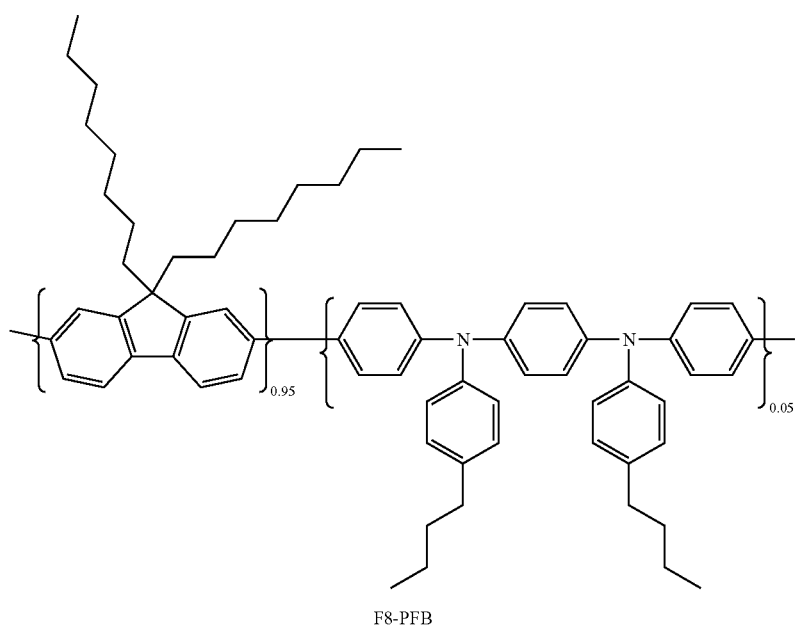

F8-PFB (2)

related phenomena in the beta-phase of poly(9,9-dioctyl) fluorene. *Physical Review B* 70, (2004)). Probes of the polyfluorene triplet population were performed at 780 nm, and the skilled person will understand how to modify this probe for other light-emitting materials based on the excited state absorption features of those materials.

Figure 9:
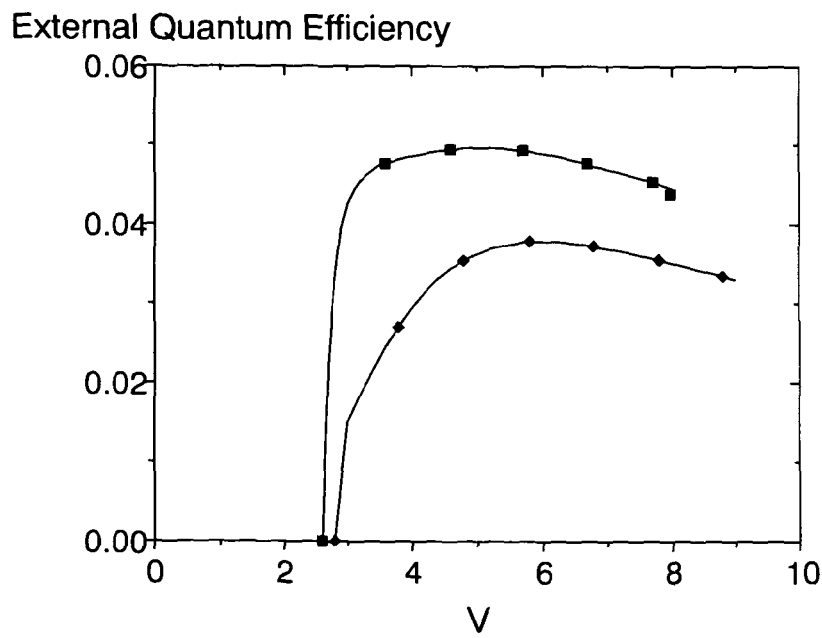
FIG. 9 is a graph of external quantum efficiency vs voltage for an exemplary device and a comparative device.

FIG. 9 shows the external quantum efficiency (EQE) of Device Example 5 (diamond), and that of a comparative device in which the triplet quenching additive is absent (square). The device with the triplet quenching additive shows a significant reduction in the peak EQE of approximately 20% at high voltage. The loss of efficiency occurs without any change to the electroluminescence spectrum of the device; therefore as would be expected from the singlet energy, the additive is neither quenching the singlet excitons nor taking part in the emission of the device. Without wishing to be bound by any theory, it is believed that the loss in efficiency is due to the removal of the TTA component caused by the quenching of the triplets from the light emitting polymer.

The density of triplet excitons on the polymer backbone is measured using quasi-cw excited state absorption as outlined above.

Figure 10:
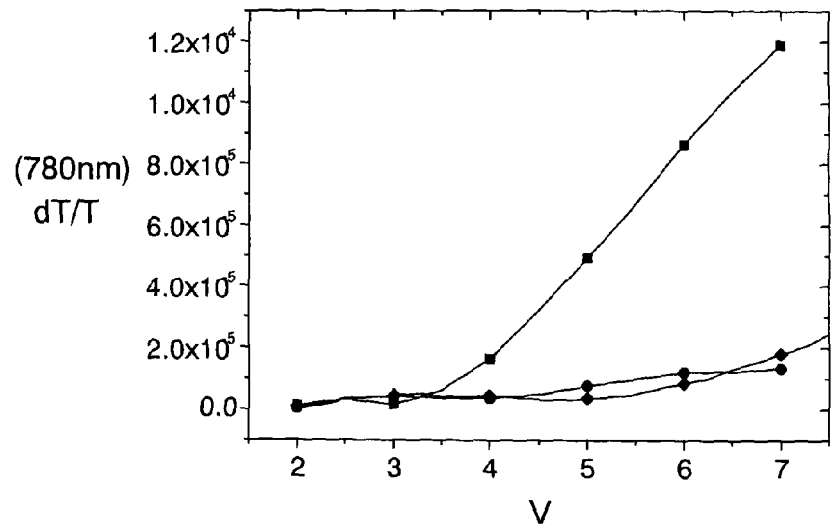
FIG. 10 is a graph illustrating triplet density for an exemplary device and a comparative device.

FIG. 10 shows the density of triplets on the polymer backbone both including (diamond, circle) and excluding (square) the triplet quencher, in the device with the additive the density of triplets on the fluorene backbone is reduced by approximately a factor of 10, thus the additive is very efficient at quenching the triplets from the polymer at all device drive voltages. Literature values for the extinction coefficient of the triplet excited state absorption in conjugated polymers range[22] from $10^{-16}$-$10^{-15}$ cm$^2$ this gives a triplet density of $10^{16}$-$10^{17}$ cm$^{-3}$ in the standard device at typical drive currents of 50 mAcm$^{-2}$ and decay is dominated by their mutual bimolecular annihilation resulting in the production of emissive singlet excitons.

Figure 11:
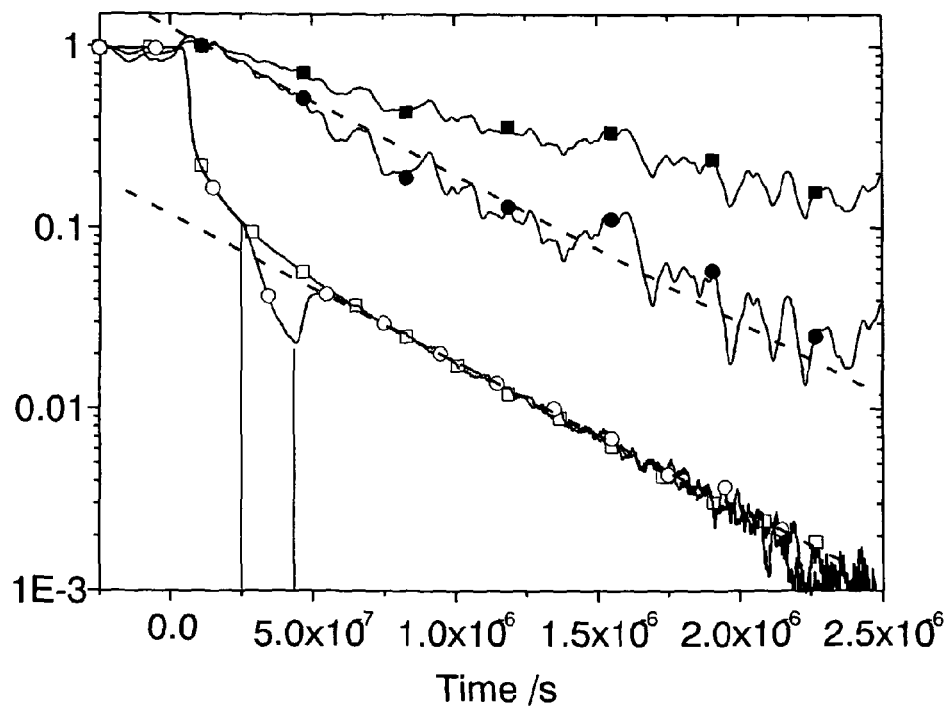
FIG. 11 is a graph of time resolved electroluminescence of an exemplary device.

FIG. 11 shows the time resolved electroluminescence (open squares, open circles) during the turn off of Device Example 2 compared with the time resolved transient triplet absorption (solid squares) and its square (solid circles). The dotted lines are of the same slope. Also shown is the effect on the electroluminescence turn off when a reverse bias pulse of −10 v 200 ns duration is applied to the device 250 ns after the device current is switched off.

After turn off of the current there is initially a rapid decay of the luminance on a similar timescale to the RC time constant of the device then a residual signal in the EL which accounts for about 30% of the total original electroluminescence and decays in a few microseconds. Generally slow transient emissions in OLEDs are ascribed to either the recombination of charges from deep traps or interfacial charge layers or TTA (see Kondakov, D. Y. Characterization of triplet-triplet annihilation in organic light-emitting diodes based on anthracene derivatives. *J. Appl. Phys.* 102, 114504-5 (2007), Sinha, S., Rothe, C., Guentner, R., Scherf, U. & Monkman, A. P. Electrophosphorescence and Delayed Electroluminescence from Pristine Polyfluorene Thin Film Devices at Low Temperature. *Physical Review Letters* 90, 127402 (2003), and Sinha, S., Monkman, A. P., Guntner, R. & Scherf, U. Space-charge-mediated delayed electroluminescence from polyfluorene thin films. *Appl. Phys. Lett.* 82, 4693-4695 (2003)).

In order to distinguish between the two mechanisms the same transient electroluminescence trace has been measured with the application of a 10 v reverse bias pulse 100 ns after the turn off of the device current, this pulse will remove, or at least perturb significantly, any trapped charge contribution to the decay of the luminance. The data shows that although emission is quenched slightly during the reverse bias pulse due to the electric field quenching of the singlet excitons the decay of EL after the reverse bias pulse is unchanged compared to the standard decay shape. One can therefore conclude that that the recombination of trapped charge is not a significant contributor to the residual luminance signal (Popovic, Z. D. & Aziz, H. Delayed electroluminescence in small-molecule-based organic light-emitting diodes: Evidence for triplet-triplet annihilation and recombination-center-mediated light-generation mechanism. *J. Appl. Phys.* 98, 013510-5 (2005)). Moreover, comparing the shape of the residual luminescence with the triplet density (shown in FIG. 11) there are two observations, firstly that the timescale of the decay of the triplets is similar to the decay of the EL but more importantly the approximate slope of the decay of the residual luminance is very similar to the slope of the square of the triplet density. This observation is strong evidence that the residual decay of the EL is due to bimolecular triplet-triplet annihilation reactions resulting in emissive singlet excitons. It is valuable to note that the triplet exciton density is not significantly quenched by the application of a 10 v reverse bias pulse because the triplets are considerably more stable than singlets to electric field due to their inherently greater exciton binding energy (Rothe, C., King, S. M. & Monkman, A. P. Electric-field-induced singlet and triplet exciton quenching in films of the conjugated polymer polyspirobifluorene. *Phys. Rev. B* 72, 085220 (2005) and Deussen, M., Scheidler, M. & Bassler, H. Electric-Field-Induced Photoluminescence Quenching in Thin-Film Light-Emitting-Diodes Based on Poly(Phenyl-P-Phenylene Vinylene). *Synth. Met.* 73, 123-129 (1995)).

Figure 12:
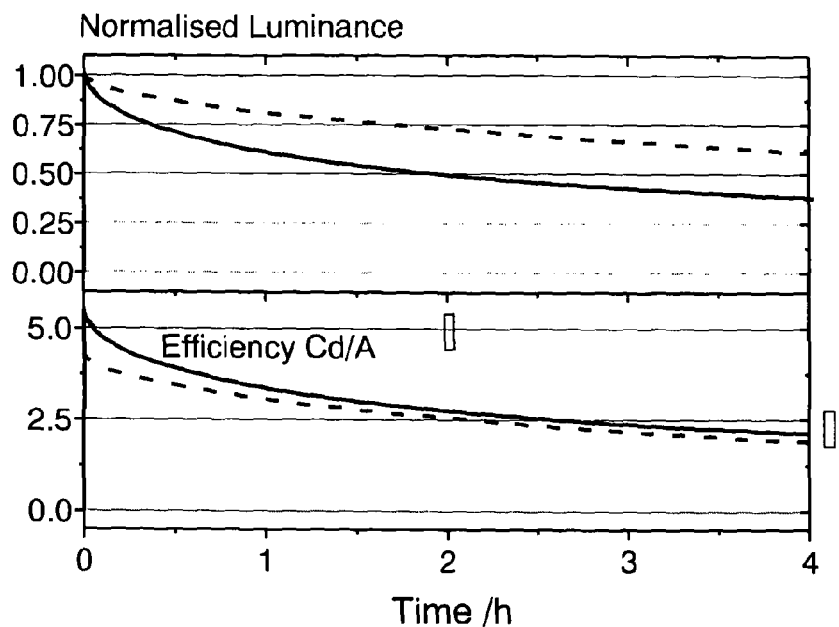
FIG. 12 is a graph of external quantum efficiency versus time for an exemplary device and a comparative device.

FIG. 12 shows the electroluminescence decay of a device both with (dotted line) and without (full line) the triplet quenching additive, the effect on the lifetime is clear, there is an improvement in T90 of approximately 5 times and an improvement of >3× to the final device lifetime. The lower panel of FIG. 5 which shows the efficiency of the devices during lifetest clearly shows that the extra efficiency boost from the TTA contribution is lost early on in the lifetest, after which the decay of the two devices is remarkably similar.

The cost to this gain in lifetime is the 20% drop in EQE from complete removal of TTA is easily outweighed by this stabilisation of the initial decay. In further arrangements, both high efficiency and lifetime may be achieved by utilising stable TTA as described above.

Device Example 6

Triplet Acceptance

A blue light-emitting polymer was prepared by Suzuki polymerisation of the following monomers using the method described in WO 00/53656:

| Monomer | Comparative Polymer 1 mol % | Polymer Example 1 mol % | Polymer Example 2 mol % |
|---|---|---|---|
| 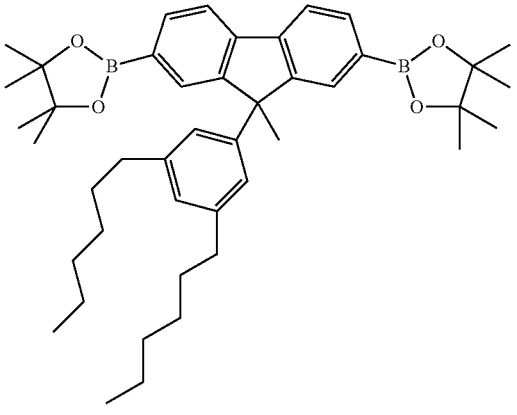 | 36 | 36 | 36 |
| 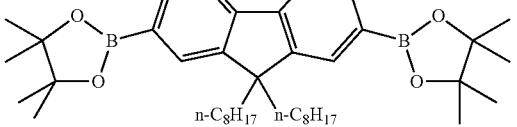 | 14 | 14 | 14 |
| 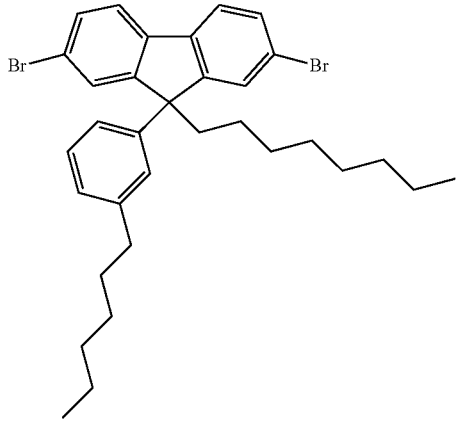 [SMILES: CCCCCCCCC1(c2cccc(CCCCCC)c2)c2cc(Br)ccc2-c2ccc(Br)cc21] | 44 | 43.65 | 43.65 |
| 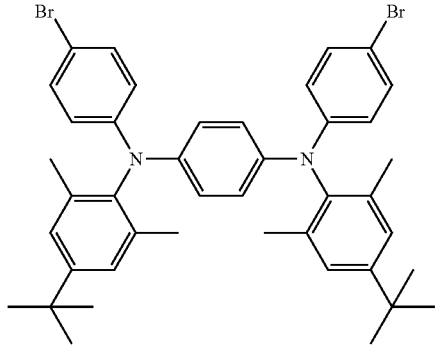 [SMILES: Cc1cc(C(C)(C)C)cc(C)c1N(c1ccc(Br)cc1)c1ccc(N(c2ccc(Br)cc2)c2c(C)cc(C(C)(C)C)cc2C)cc1] | 5 | 5 | 5 |

-continued
| Monomer | Comparative Polymer 1 mol % | Polymer Example 1 mol % | Polymer Example 2 mol % |
|---|---|---|---|
| ![phenoxazine monomer] | 1 | 1 | 1 |
| Triplet quenching monomer (1) | 0 | 0.35 | 0. |
| Triplet quenching monomer (2) | 0 | 0 | 0.35 |
Asymmetrically substituted fluorene-containing monomers were prepared according to the following schemes:
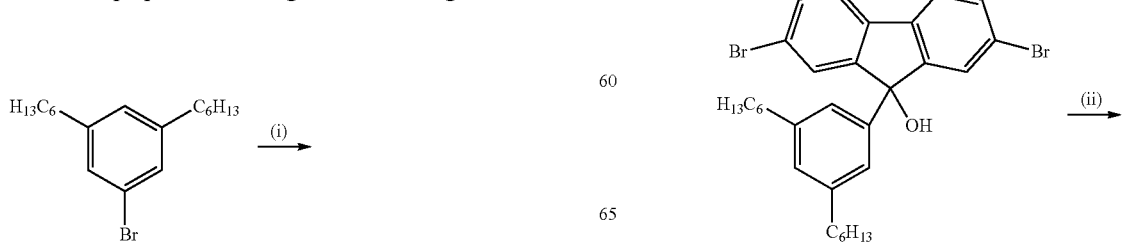

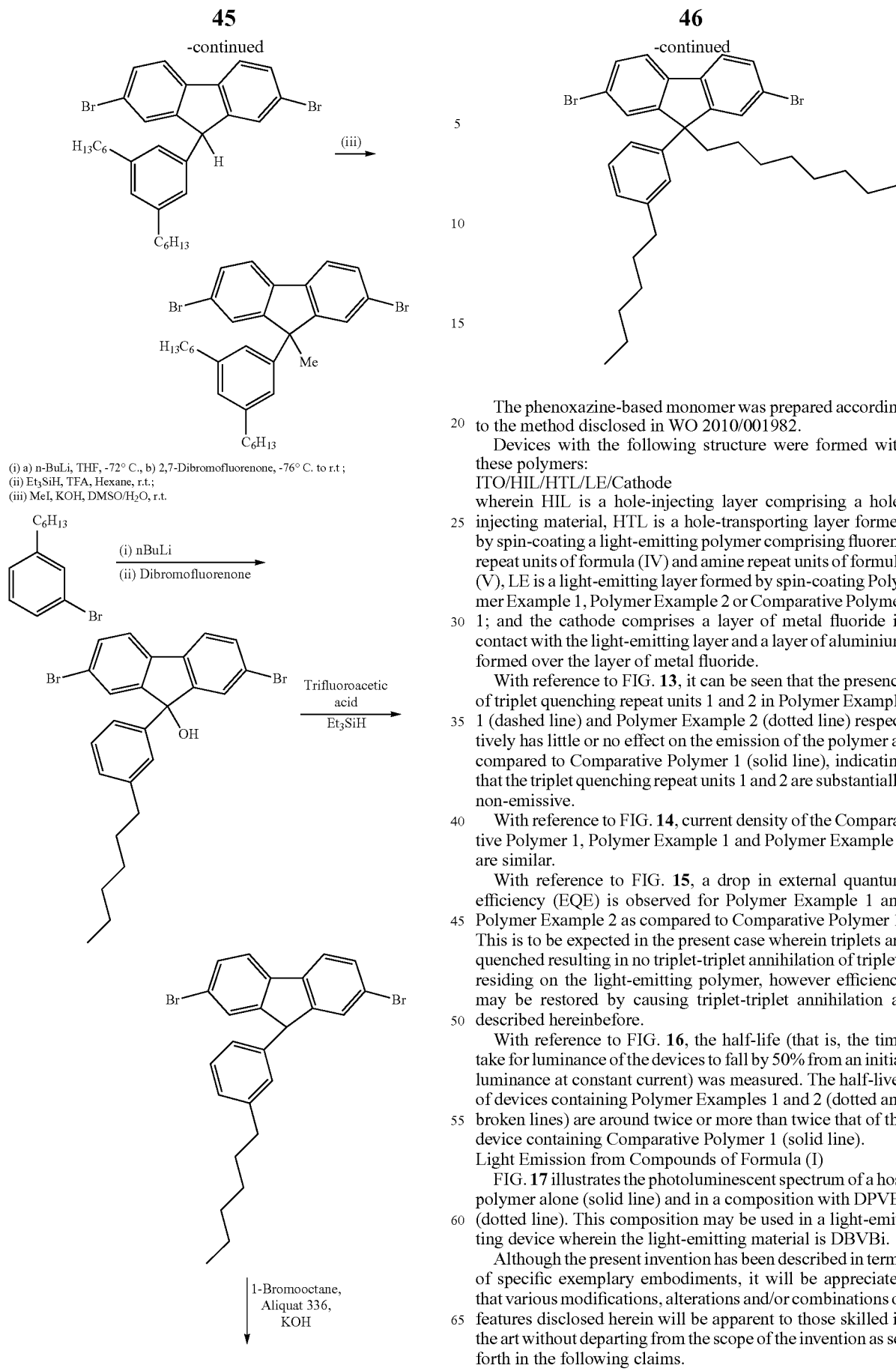

The phenoxazine-based monomer was prepared according to the method disclosed in WO 2010/001982.

Devices with the following structure were formed with these polymers:

ITO/HIL/HTL/LE/Cathode wherein HIL is a hole-injecting layer comprising a hole-injecting material, HTL is a hole-transporting layer formed by spin-coating a light-emitting polymer comprising fluorene repeat units of formula (IV) and amine repeat units of formula (V), LE is a light-emitting layer formed by spin-coating Polymer Example 1, Polymer Example 2 or Comparative Polymer 1; and the cathode comprises a layer of metal fluoride in contact with the light-emitting layer and a layer of aluminium formed over the layer of metal fluoride.

Figure 13:
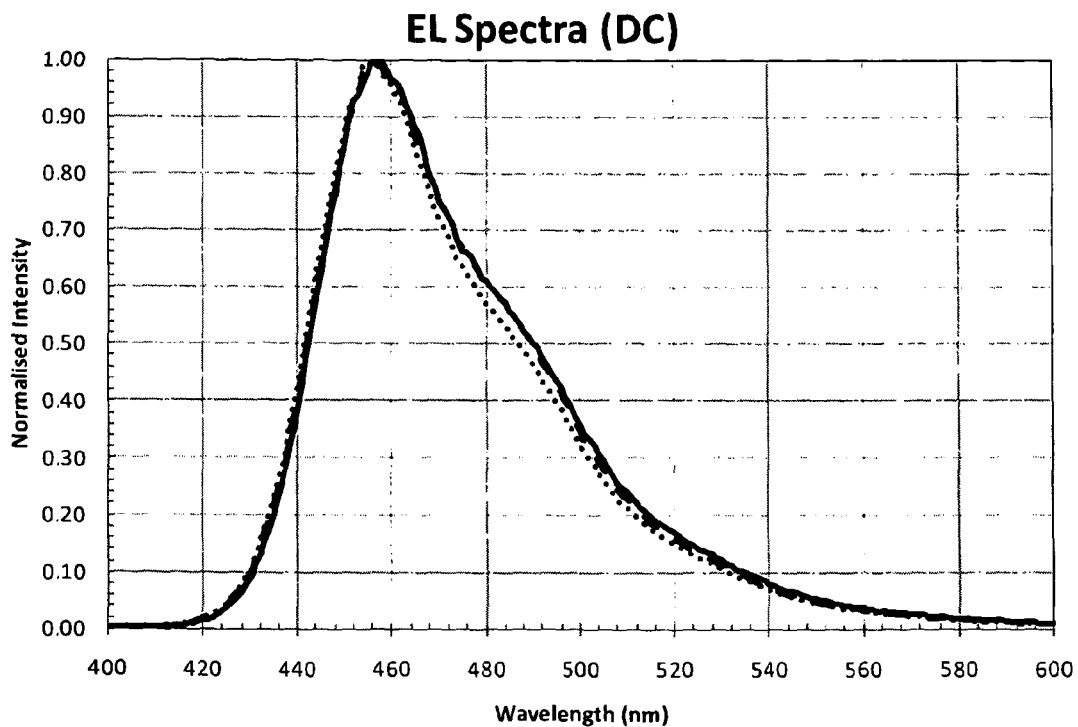
FIG. 13 is a graph of electroluminescence of two exemplary devices and a comparative device.

With reference to FIG. 13, it can be seen that the presence of triplet quenching repeat units 1 and 2 in Polymer Example 1 (dashed line) and Polymer Example 2 (dotted line) respectively has little or no effect on the emission of the polymer as compared to Comparative Polymer 1 (solid line), indicating that the triplet quenching repeat units 1 and 2 are substantially non-emissive.

Figure 14:
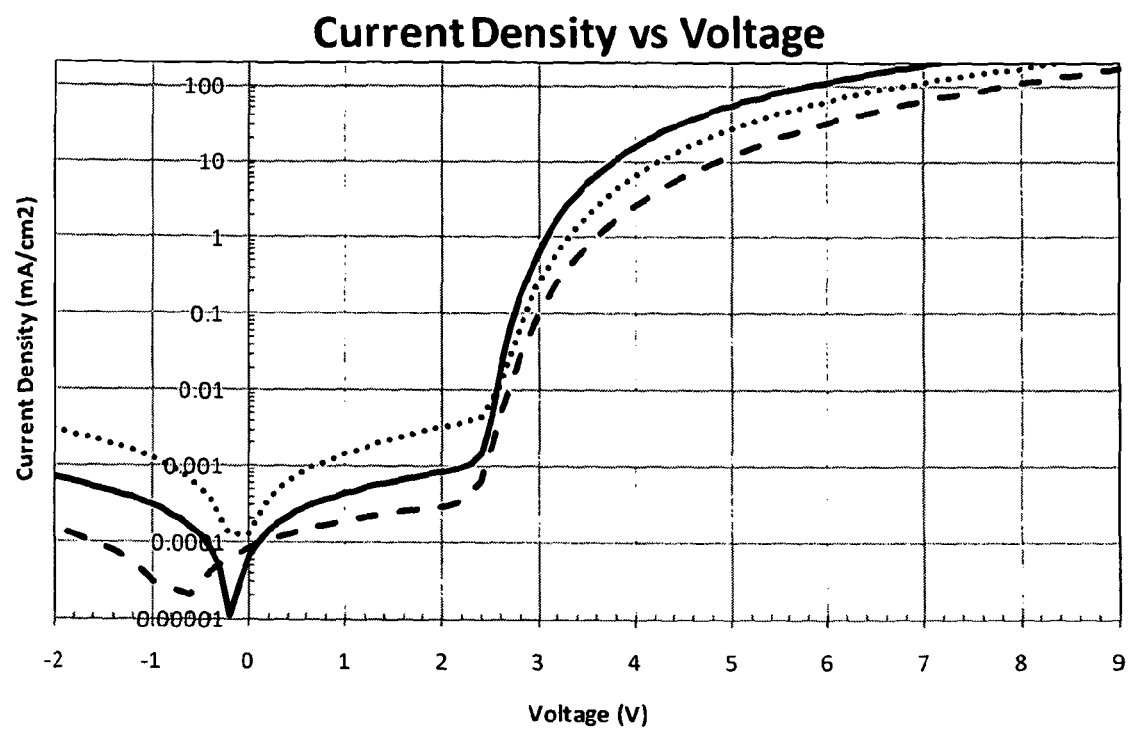
FIG. 14 is a graph of current density vs. voltage for the exemplary devices and comparative device of FIG. 13.

With reference to FIG. 14, current density of the Comparative Polymer 1, Polymer Example 1 and Polymer Example 2 are similar.

Figure 15:
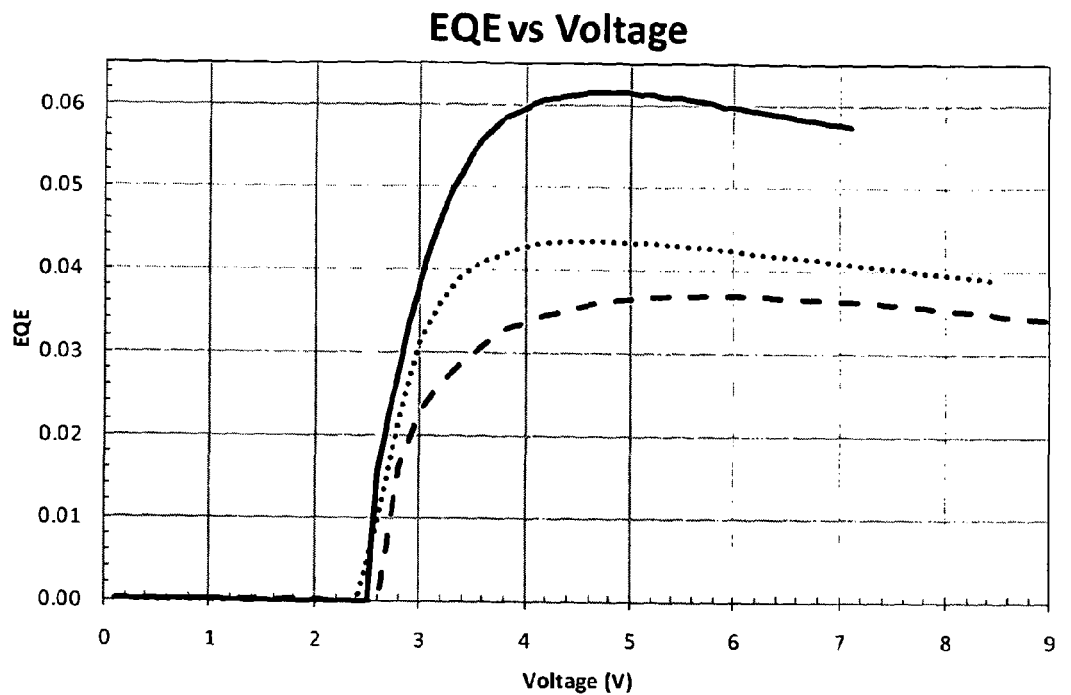
FIG. 15 is a graph of external quantum efficiency vs. voltage for the exemplary devices and comparative device of FIGS. 13 and 14.

With reference to FIG. 15, a drop in external quantum efficiency (EQE) is observed for Polymer Example 1 and Polymer Example 2 as compared to Comparative Polymer 1. This is to be expected in the present case wherein triplets are quenched resulting in no triplet-triplet annihilation of triplets residing on the light-emitting polymer, however efficiency may be restored by causing triplet-triplet annihilation as described hereinbefore.

Figure 16:
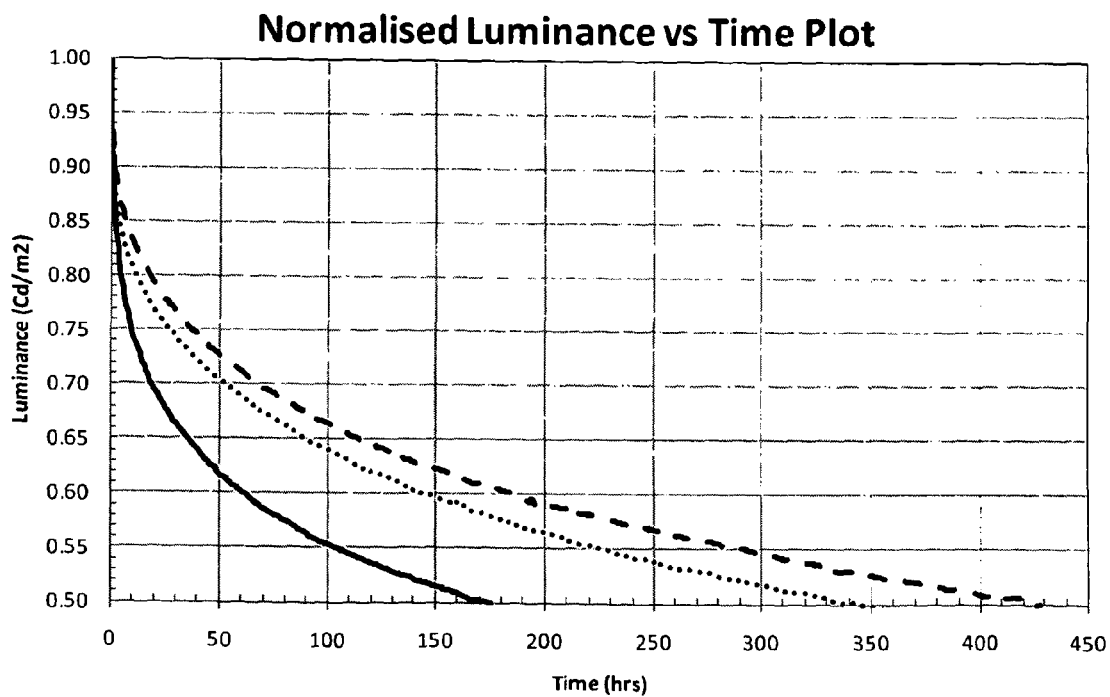
FIG. 16 is a graph illustrating the lifetime of the exemplary devices and comparative device of FIGS. 13, 14 and 15.

With reference to FIG. 16, the half-life (that is, the time take for luminance of the devices to fall by 50% from an initial luminance at constant current) was measured. The half-lives of devices containing Polymer Examples 1 and 2 (dotted and broken lines) are around twice or more than twice that of the device containing Comparative Polymer 1 (solid line).

Light Emission from Compounds of Formula (I)

Figure 17:
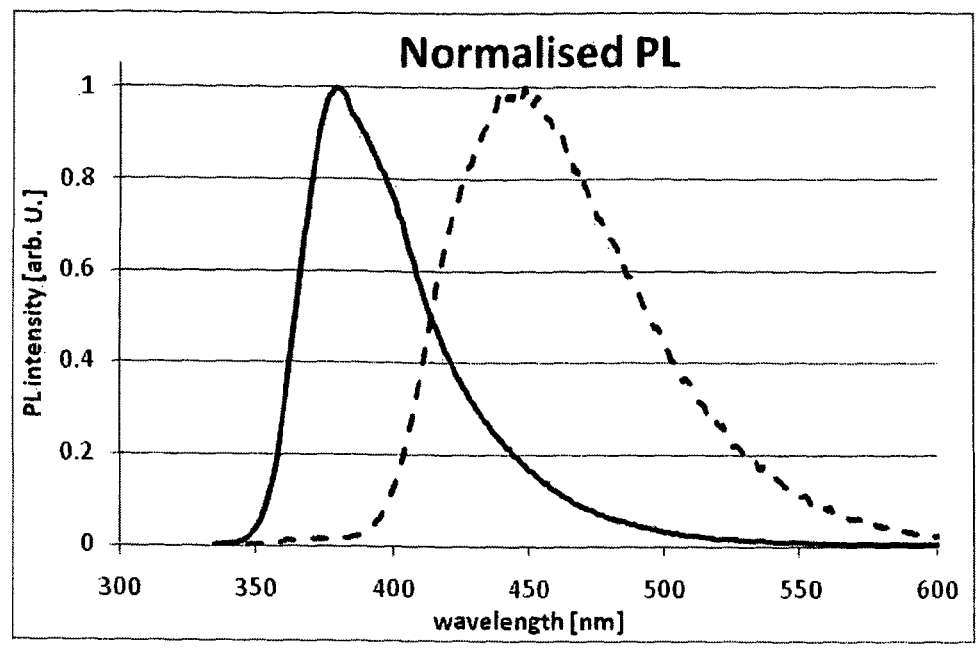
FIG. 17 illustrates a photoluminescence spectrum of an exemplary composition of the invention.

FIG. 17 illustrates the photoluminescent spectrum of a host polymer alone (solid line) and in a composition with DPVBi (dotted line). This composition may be used in a light-emitting device wherein the light-emitting material is DBVBi.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A fluorescent light-emitting polymer comprising a fluorescent light-emitting repeat unit and a triplet-accepting repeat unit having a triplet energy level lower than the triplet energy level of the light-emitting repeat unit, wherein the triplet-accepting repeat unit has the formula:

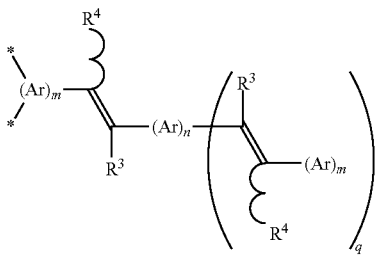

wherein each Ar independently represents an optionally substituted aryl or heteroaryl group; at least one Ar group is phenyl; n is 1; m is 1-5; q is 0; $R^3$ is phenyl; $R^4$ is selected from H or a substituent; in the case where $R^4$ is not H, $R^4$ and $(Ar)_m$ bound to the same carbon atom are optionally linked by a direct bond or a divalent group and $(Ar)_m$ are optionally linked by a direct bond or a divalent group; adjacent Ar groups are optionally linked by a divalent group in the case where m is at least 2; and $R^3$ is linked to $(Ar)_n$ by a direct bond.

2. A polymer according to claim 1, wherein the divalent linking group linking any of adjacent Ar groups, or $R^4$ and $(Ar)_m$, is selected from —$(CR^5R^6)_p$—, —$(SiR^5R^6)_p$—, O, $NR^5$, and $PR^5$, wherein $R^5$ and $R^6$ are each independently selected from H or a substituent and p is 1-5.

3. A polymer according to claim 2, wherein $R^5$ and $R^6$ are each independently selected from H or a substituent selected from alkyl, wherein one or more non-adjacent C atoms are optionally replaced with O, S, substituted N, C=O, and/or —COO—, and wherein one or more H atoms are optionally replaced with F; or aryl, heteroaryl, arylalkyl, or heteroarylalkyl, each of which may optionally be substituted with halogen, cyano, or alkyl wherein one or more non-adjacent C atoms are optionally replaced with O, S, substituted N, C=O, and/or —COO—.

4. A polymer according to claim 2, wherein p is 1 or 2.

5. A polymer according to claim 1, wherein all Ar groups are phenyl.

6. A polymer according to claim 1, wherein $R^4$ is phenyl.

7. A polymer according to claim 1, wherein $R^3$ and $(Ar)_n$ are linked to form an optionally substituted fluorene.

8. A polymer according to claim 1, wherein at least one Ar group is substituted with at least one substituent selected from halogen; cyano; alkyl, wherein one or more non-adjacent C atoms are optionally replaced with O, S, substituted N, C=O, and/or —COO—; and —$(Ar^4)_z$, wherein $Ar^4$ in each occurrence is independently selected from optionally substituted aryl or heteroaryl and z is at least 1, and wherein a plurality of $Ar^4$ groups are optionally linked to form a straight or branched chain of $Ar^4$ groups in the case where z is greater than 1.

9. A polymer according to claim 8, wherein z is 1, 2, or 3.

10. A polymer according to claim 1, wherein at least one meta-position of at least one terminal Ar group is substituted with a substituent selected from halogen; cyano; alkyl, wherein one or more non-adjacent C atoms are optionally replaced with O, S, substituted N, C=O, and/or —COO—; and —$(Ar^4)_z$, wherein $Ar^4$ in each occurrence is independently selected from optionally substituted aryl or heteroaryl and z is at least 1, and wherein a plurality of $Ar^4$ groups are optionally linked to form a straight or branched chain of $Ar^4$ groups in the case where z is greater than 1.

11. A polymer according to claim 10, wherein z is 1, 2, or 3.

12. A polymer according to claim 1 comprising amine repeat units.

13. A polymer according claim 1, wherein the triplet-accepting material is present in an amount of at least 0.05 mol %.

14. A polymer according claim 13, wherein the triplet-accepting material is present in an amount of at least 0.1 mol %.

15. A polymer according to claim 1, wherein the triplet-accepting repeat unit has one of the following structures:

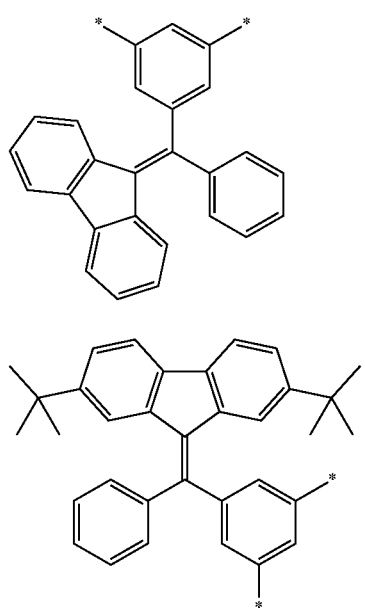

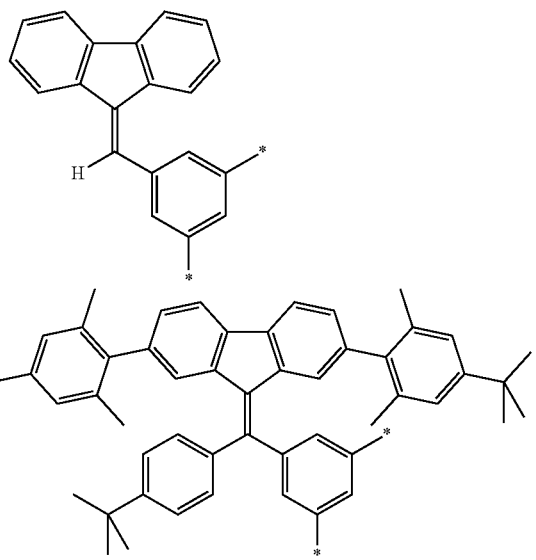

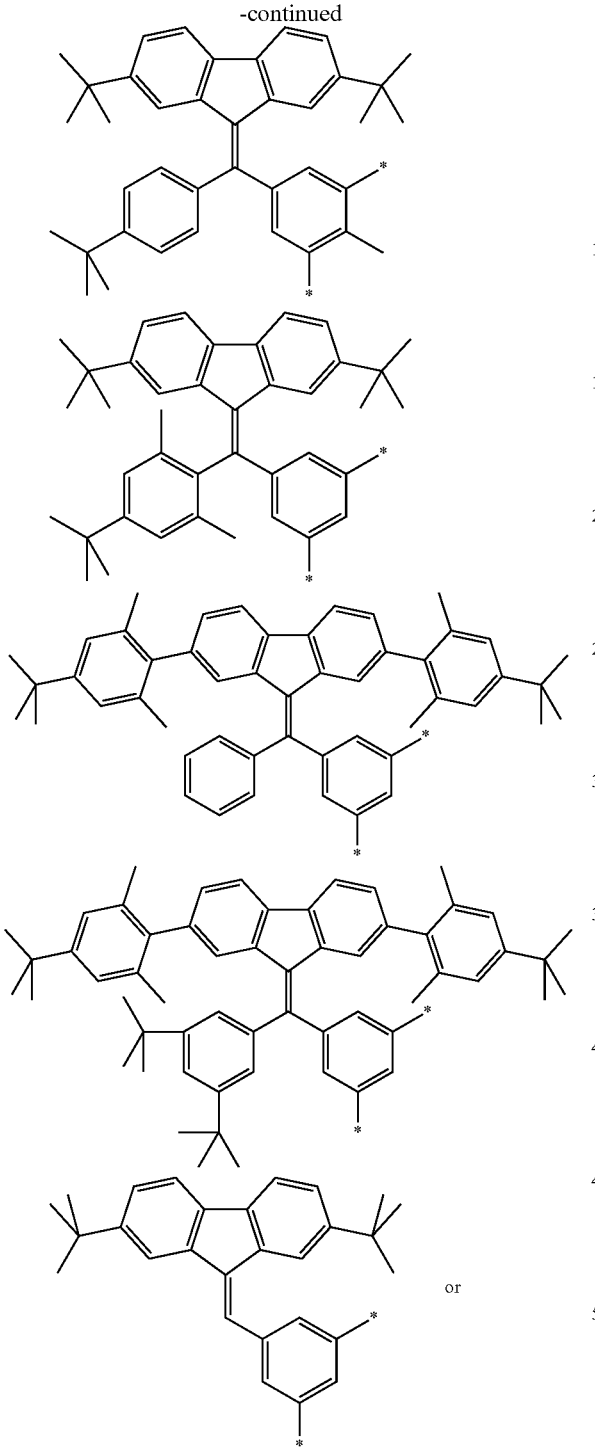

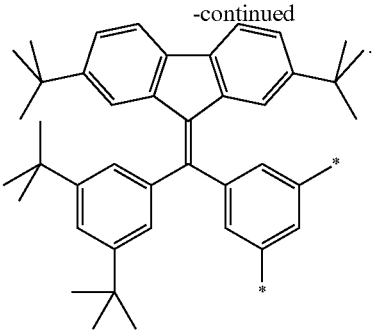

16. A solution comprising a solvent and a polymer according to claim 1.

17. An organic light-emitting device comprising an anode, a cathode, a light-emitting layer between the anode and cathode, and optionally one or more layers selected from charge transporting and charge-blocking layers between the anode and cathode, wherein at least one of the light-emitting layer and the one or more optional layers comprises a polymer according to claim 1.

18. A method of forming an organic light-emitting device according to claim 17 comprising the steps of:
depositing a solution comprising a solvent and a polymer comprising a fluorescent light-emitting repeat unit and a triplet-accepting repeat unit having a triplet energy level lower than the triplet energy level of the light-emitting repeat unit, wherein the triplet-accepting repeat unit has the formula:

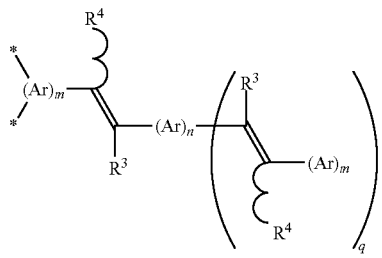

wherein each Ar independently represents an optionally substituted aryl or heteroaryl group; at least one Ar group is phenyl; n is 1; m is 1-5; q is 0; $R^3$ is phenyl; $R^4$ is selected from H or a substituent; in the case where $R^4$ is not H, $R^4$ and $(Ar)_m$ bound to the same carbon atom are optionally linked by a direct bond or a divalent group; and $(Ar)_m$ are optionally linked by a direct bond or a divalent group; adjacent Ar groups are optionally linked by a divalent group in the case where m is at least 2; and $R^3$ is linked to $(Ar)_n$ by a direct bond, and evaporating the solvent.

* * * * *